(12) United States Patent
Shelton, IV et al.

(10) Patent No.: US 12,718,044 B2
(45) Date of Patent: Aug. 25, 2026

(54) SYSTEMS AND METHODS FOR STORAGE AND TRANSFER OF SMART PACKAGING METADATA

(71) Applicant: Cilag GmbH International, Zug (CH)

(72) Inventors: Frederick E. Shelton, IV, Cincinnati, OH (US); Jacqueline C. Aronhalt, Loveland, OH (US); Brian Schings, Maineville, OH (US); Gregory J. Bakos, Mason, OH (US); Jason Rector, Maineville, OH (US); Matthew D. Cowperthwait, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 165 days.

(21) Appl. No.: 18/479,470

(22) Filed: Oct. 2, 2023

(65) Prior Publication Data

US 2025/0014735 A1 Jan. 9, 2025

Related U.S. Application Data

(60) Provisional application No. 63/525,572, filed on Jul. 7, 2023.

(51) Int. Cl.
*G16H 40/67* (2018.01)
*A61B 50/30* (2016.01)
(Continued)

(52) U.S. Cl.
CPC .......... *G06K 17/0029* (2013.01); *A61B 50/30* (2016.02); *A61B 90/98* (2016.02);
(Continued)

(58) Field of Classification Search
None
See application file for complete search history.

(56) References Cited

U.S. PATENT DOCUMENTS 6,428,867 B1 8/2002 Scott et al.
6,861,954 B2 3/2005 Levin
(Continued)

FOREIGN PATENT DOCUMENTS

CA 2593679 A1 12/2008
CA 2725727 A1 12/2009
(Continued)

OTHER PUBLICATIONS

U.S. Appl. No. 18/479,461, filed Oct. 2, 2023, Frederick E. Shelton IV et al.

(Continued)

*Primary Examiner* — John A Pauls
(74) *Attorney, Agent, or Firm* — Condo Roccia Koptiw LLP

(57) ABSTRACT

Systems and methods are provided. The systems include a manufacturer-sealed sterile surgical packaging containing a surgical instrument configured to be used in a surgical procedure, a graphical display, at least one data processor in operable communication with the graphical display, and memory in operable communication with the at least one data processor, and storing instructions configured to cause the at least one data processor to perform operations. The operations can include recording historical data points of the surgical instrument, determining a degradation level of the surgical instrument based on the historical data point, determining an altered set of operating parameters based on the degradation level of the surgical instrument, and providing the altered set of operating parameters.

17 Claims, 16 Drawing Sheets

(51) Int. Cl.

| | |
|---|---|
| ***A61B 90/98*** | (2016.01) |
| ***A61J 1/18*** | (2023.01) |
| ***G05B 13/02*** | (2006.01) |
| ***G06K 7/10*** | (2006.01) |
| ***G06K 17/00*** | (2006.01) |
| ***G06K 19/07*** | (2006.01) |
| ***G06K 19/077*** | (2006.01) |
| ***G06Q 10/0832*** | (2023.01) |
| ***G06Q 10/0833*** | (2023.01) |
| ***G06Q 30/018*** | (2023.01) |
| ***G08B 5/36*** | (2006.01) |
| ***G09G 3/34*** | (2006.01) |
| ***G16H 40/20*** | (2018.01) |
| ***G16H 40/40*** | (2018.01) |
| ***G16H 40/63*** | (2018.01) |
| ***H04W 4/029*** | (2018.01) |
| *G16H 20/40* | (2018.01) |

(52) U.S. Cl.

CPC .............. *A61J 1/18* (2013.01); *G05B 13/024* (2013.01); *G06K 7/10099* (2013.01); *G06K 19/0723* (2013.01); *G06K 19/07749* (2013.01); *G06Q 10/0832* (2013.01); *G06Q 10/0833* (2013.01); *G06Q 30/018* (2013.01); *G08B 5/36* (2013.01); *G09G 3/344* (2013.01); *G16H 40/20* (2018.01); *G16H 40/40* (2018.01); *G16H 40/63* (2018.01); *G16H 40/67* (2018.01); *H04W 4/029* (2018.02); *G09G 2380/04* (2013.01); *G16H 20/40* (2018.01)

(56) References Cited

U.S. PATENT DOCUMENTS 7,256,696 B2 8/2007 Levin
7,518,502 B2 4/2009 Austin et al.
7,738,971 B2 6/2010 Swayze et al.
7,932,826 B2 4/2011 Fritchie et al.
8,248,232 B2 8/2012 Stevenson et al.
8,253,555 B2 8/2012 Stevenson et al.
8,269,629 B2 9/2012 Lyon et al.
8,397,971 B2 3/2013 Yates et al.
8,414,577 B2 4/2013 Boudreaux et al.
8,533,075 B1 9/2013 Sayers, III et al.
8,756,124 B1 6/2014 Sayers, III et al.
9,000,720 B2 4/2015 Stulen et al.
9,017,851 B2 4/2015 Felder et al.
9,375,303 B1 6/2016 Cook et al.
9,414,893 B2 8/2016 Jacobson
9,489,785 B2 11/2016 Klammer et al.
9,514,341 B2 12/2016 Blair et al.
9,571,143 B2 2/2017 Richley
9,622,808 B2 4/2017 Beller et al.
9,717,565 B2 8/2017 Blair
9,763,725 B2 9/2017 McPherson et al.
9,826,977 B2 11/2017 Leimbach et al.
9,918,906 B2 3/2018 Chaturvedi et al.
10,010,636 B2 7/2018 Henniges et al.
10,080,813 B2 9/2018 Felder et al.
10,452,875 B2 10/2019 Forster et al.
10,806,850 B2 10/2020 Patel et al.
11,051,806 B2 7/2021 Vendely et al.
11,123,074 B2 9/2021 Adams et al.
11,259,803 B2 3/2022 Shelton, IV et al.
11,268,311 B1 3/2022 Tong
11,311,306 B2 4/2022 Shelton, IV et al.
11,321,652 B1 5/2022 Mahmood
11,426,167 B2 8/2022 Shelton, IV et al.
11,481,739 B1 10/2022 Mckinzie
11,523,822 B2 12/2022 Shelton, IV et al.
11,544,235 B2 1/2023 Fish et al.
11,607,216 B2 3/2023 Krulevitch et al.
11,771,419 B2 10/2023 Shelton, IV et al.
11,786,240 B2 10/2023 Shelton, IV et al.
11,954,627 B2 4/2024 Mahmood
11,968,205 B1 4/2024 Mousseau et al.
12,164,985 B1 12/2024 Shelton, IV et al.
12,220,198 B2 2/2025 Aman et al.
2006/0143645 A1 6/2006 Vock et al.
2006/0244593 A1 11/2006 Nycz et al.
2007/0017535 A1 1/2007 Frank et al.
2007/0083286 A1 4/2007 Kobayashi
2007/0272746 A1 11/2007 Ortiz et al.
2008/0021307 A1 1/2008 Freeman et al.
2008/0030345 A1 2/2008 Austin et al.
2008/0042823 A1 2/2008 Heasley et al.
2008/0054073 A1 3/2008 Charles et al.
2008/0061153 A1 3/2008 Hickle et al.
2008/0150722 A1 6/2008 Jackson
2008/0266057 A1 10/2008 Erickson et al.
2009/0015196 A1 1/2009 Baxter et al.
2009/0143734 A1 6/2009 Humayun et al.
2009/0267765 A1 10/2009 Greene et al.
2009/0289776 A1 11/2009 Moore et al.
2010/0108761 A1 5/2010 Nycz et al.
2010/0118138 A1 5/2010 Djachiachvili
2010/0161345 A1 6/2010 Cain et al.
2010/0174415 A1 7/2010 Humayun et al.
2010/0193569 A1 8/2010 Yates et al.
2010/0219238 A1 9/2010 Mallett et al.
2010/0311385 A1 12/2010 Hurwitz
2011/0100139 A1 5/2011 Parikh
2011/0313894 A1 12/2011 Dye et al.
2012/0110824 A1 5/2012 Smith et al.
2012/0111591 A1 5/2012 Shelton, IV et al.
2012/0112690 A1 5/2012 Stulen et al.
2012/0209165 A1 8/2012 Degen et al.
2013/0087610 A1 4/2013 Shin et al.
2013/0247194 A1 9/2013 Jha et al.
2013/0268113 A1 10/2013 Sandvik et al.
2013/0293353 A1* 11/2013 McPherson ............ A61B 50/30
340/10.1
2013/0304143 A1 11/2013 Banville
2014/0057619 A1 2/2014 Chen
2014/0081659 A1 3/2014 Nawana et al.
2014/0266713 A1 9/2014 Sehgal et al.
2014/0276665 A1 9/2014 Lopez et al.
2014/0288952 A1 9/2014 Smith et al.
2014/0306807 A1 10/2014 Rowland et al.
2014/0353188 A1 12/2014 Reschke et al.
2014/0378952 A1 12/2014 Humayun et al.
2015/0169829 A1 6/2015 Jaynes
2015/0278758 A1 10/2015 Kim et al.
2015/0302157 A1 10/2015 Collar et al.
2015/0374868 A1 12/2015 Bruce et al.
2016/0012182 A1* 1/2016 Golay .................... G16H 40/20
705/3
2016/0022361 A1 1/2016 Khajavi
2016/0200515 A1 7/2016 Sandvik et al.
2016/0211688 A1 7/2016 Orr et al.
2016/0243318 A1* 8/2016 Despa ............... A61M 5/14248
2016/0253472 A1 9/2016 Pedersen et al.
2016/0310134 A1 10/2016 Contini et al.
2017/0068788 A1 3/2017 Cannady et al.
2017/0173262 A1 6/2017 Veltz
2017/0188864 A1 7/2017 Drury
2017/0224859 A1 8/2017 Broninx et al.
2017/0255479 A1* 9/2017 Dannaher ...... A61B 17/320068
2017/0258401 A1 9/2017 Volpe
2017/0284860 A1 10/2017 Dickerson
2017/0312044 A1 11/2017 Conlon et al.
2017/0319386 A1 11/2017 Humayun et al.
2017/0329911 A1 11/2017 Khajavi
2018/0153639 A1 6/2018 Wehrle et al.
2018/0168690 A1 6/2018 Uthgenannt et al.
2018/0183874 A1 6/2018 Cook
2018/0289434 A1 10/2018 Palo et al.
2019/0059997 A1 2/2019 Frushour
2019/0217018 A1 7/2019 Bauss et al.
2019/0287055 A1 9/2019 Wicks et al.
2020/0100825 A1 4/2020 Henderson et al.
2020/0214776 A1* 7/2020 Hingwe ................. A61B 90/98

(56) References Cited

U.S. PATENT DOCUMENTS

| | | | |
|---|---|---|---|
| 2020/0279217 | A1 | 9/2020 | Gravelle et al. |
| 2020/0405290 | A1 | 12/2020 | Shelton, IV et al. |
| 2020/0405311 | A1 | 12/2020 | Shelton, IV et al. |
| 2020/0405409 | A1 | 12/2020 | Shelton, IV et al. |
| 2020/0405441 | A1 | 12/2020 | Shelton, IV et al. |
| 2020/0410177 | A1 | 12/2020 | Shelton, IV |
| 2020/0410180 | A1 | 12/2020 | Shelton, IV et al. |
| 2021/0019581 | A1 | 1/2021 | Halvorsen et al. |
| 2021/0060243 | A1 | 3/2021 | Dave et al. |
| 2021/0184334 | A1 | 6/2021 | Weyn et al. |
| 2021/0315655 | A1 | 10/2021 | Lenzenhuber et al. |
| 2021/0345952 | A1 | 11/2021 | Harris et al. |
| 2021/0345953 | A1 | 11/2021 | Shelton, IV et al. |
| 2021/0346015 | A1 | 11/2021 | Krulevitch et al. |
| 2021/0350895 | A1 | 11/2021 | Bakos et al. |
| 2021/0350896 | A1 | 11/2021 | Shelton, IV et al. |
| 2021/0350897 | A1 | 11/2021 | Shelton, IV et al. |
| 2022/0101991 | A1 | 3/2022 | Sowards et al. |
| 2022/0125543 | A1 | 4/2022 | Birkbeck et al. |
| 2022/0174943 | A1 | 6/2022 | Skiba et al. |
| 2022/0202535 | A2 | 6/2022 | Erskine-smith |
| 2022/0227535 | A1 | 7/2022 | Benjamin |
| 2022/0240770 | A1 | 8/2022 | Sagiv et al. |
| 2022/0257105 | A1 | 8/2022 | Sagiv et al. |
| 2022/0273304 | A1 | 9/2022 | Shelton, IV et al. |
| 2022/0304560 | A1 | 9/2022 | Jackson et al. |
| 2022/0313145 | A1 | 10/2022 | Shelton, IV et al. |
| 2022/0313255 | A1 | 10/2022 | Shelton, IV et al. |
| 2022/0313256 | A1 | 10/2022 | Shelton, IV et al. |
| 2022/0354617 | A1 | 11/2022 | Boehler et al. |
| 2022/0374807 | A1 | 11/2022 | Mahmood |
| 2022/0378662 | A1 | 12/2022 | Petersen et al. |
| 2023/0023083 | A1 | 1/2023 | Shelton, IV et al. |
| 2023/0027543 | A1 | 1/2023 | Shelton, IV et al. |
| 2023/0032422 | A1 | 2/2023 | Lowry et al. |
| 2023/0054586 | A1 | 2/2023 | Roh et al. |
| 2023/0104580 | A1 | 4/2023 | Roh et al. |
| 2023/0128550 | A1 | 4/2023 | Leung et al. |
| 2023/0137578 | A1 | 5/2023 | Cella et al. |
| 2023/0222454 | A1 | 7/2023 | Cella et al. |
| 2023/0352160 | A1 | 11/2023 | Suzuki et al. |
| 2023/0381425 | A1 | 11/2023 | Rajagopalan et al. |
| 2023/0414140 | A1 | 12/2023 | Li et al. |
| 2024/0049958 | A1 | 2/2024 | Sagiv et al. |
| 2024/0124216 | A1 | 4/2024 | Girault |
| 2024/0267372 | A1 | 8/2024 | Mousseau et al. |
| 2024/0289715 | A1 | 8/2024 | Mahmood |

FOREIGN PATENT DOCUMENTS

| | | | |
|---|---|---|---|
| CN | 106532826 | A | 3/2017 |
| CN | 111104995 | A | 5/2020 |
| CN | 112912029 | A | 6/2021 |
| CN | 113335790 | A | 9/2021 |
| EP | 3842689 | A1 | 6/2021 |
| EP | 3842689 | B1 | 5/2024 |
| JP | 2002166261 | A | 6/2002 |
| JP | 2007145383 | A | 6/2007 |
| JP | 2008171446 | A | 7/2008 |
| JP | 6542317 | B2 | 6/2019 |
| WO | 0245874 | A1 | 6/2002 |
| WO | 2006026289 | A1 | 3/2006 |
| WO | 2016148923 | A1 | 9/2016 |
| WO | 2017035474 | A1 | 3/2017 |
| WO | WO-2018010931 | A1 | 1/2018 |
| WO | 2019192027 | A1 | 10/2019 |
| WO | 2020006766 | A1 | 1/2020 |
| WO | 2021055590 | A1 | 3/2021 |
| WO | 2022208294 | A1 | 10/2022 |

OTHER PUBLICATIONS

U.S. Appl. No. 18/479,487, filed Oct. 2, 2023, Jacqueline C. Aronhalt et al.

U.S. Appl. No. 18/479,489, filed Oct. 2, 2023, Jacqueline C. Aronhalt et al.

U.S. Appl. No. 18/479,495, filed Oct. 2, 2023, Jacqueline C. Aronhalt et al.

U.S. Appl. No. 18/452,928, filed Aug. 21, 2023, Shane R. Adams et al.

U.S. Appl. No. 18/452,932, filed Aug. 21, 2023, Frederick E. Shelton IV et al.

U.S. Appl. No. 18/452,938, filed Aug. 21, 2023, Frederick E. Shelton IV et al.

U.S. Appl. No. 18/452,948, filed Aug. 21, 2023, Frederick E. Shelton IV et al.

U.S. Appl. No. 18/452,953, filed Aug. 21, 2023, Frederick E. Shelton IV et al.

U.S. Appl. No. 18/452,956, filed Aug. 21, 2023, Frederick E. Shelton IV et al.

U.S. Appl. No. 18/452,960, filed Aug. 21, 2023, Frederick E. Shelton IV et al.

U.S. Appl. No. 18/226,501, filed Jul. 26, 2023, Frederick E. Shelton IV et al.

U.S. Appl. No. 18/226,505, filed Jul. 26, 2023, Frederick E. Shelton IV et al.

U.S. Appl. No. 18/226,511, filed Jul. 26, 2023, Frederick E. Shelton IV et al.

"International Search Report and Written Opinion received for PCT Application No. PCT/IB2024/056612", Oct. 9, 2024, 10 pages.

"International Search Report and Written Opinion received for PCT Application No. PCT/IB2024/056614", Oct. 11, 2024, 17 pages.

"International Search Report and Written Opinion received for PCT Application No. PCT/IB2024/056618", Oct. 8, 2024, 16 pages.

"International Search Report and Written Opinion received for PCT Application No. PCT/IB2024/056622", Oct. 7, 2024, 12 pages.

"International Search Report and Written Opinion received for PCT Application No. PCT/IB2024/056623", Oct. 28, 2024, 17 pages.

"International Search Report and Written Opinion received for PCT Application No. PCTIB2024056629", Oct. 24, 2024, 11 pages.

"International Search Report and Written Opinion, received for PCT Application No. PCT/IB2024/056611", Aug. 21, 2024.

"International Search Report and Written Opinion, received for PCT Application No. PCT/IB2024/056615", Nov. 5, 2024, 12 pages.

"International Search Report and Written Opinion, received for PCT Application No. PCT/IB2024/056619", Oct. 9, 2024, 11 pages.

"International Search Report and Written Opinion, received for PCT Application No. PCT/IB2024/056620", Sep. 23, 2024, 12 pages.

"International Search Report and Written Opinion, received for PCT Application No. PCT/IB2024/056631", Oct. 14, 2024, 12 pages.

"International Search Report and Written Opinion, received for PCT Application No. PCT/IB2024/056633", Sep. 19, 2024, 13 pages.

"International Search Report and Written Opinion, received for PCT Application No. PCT/IB2024/056627", Oct. 8, 2024, 13 pages.

"Understanding the Requirements of ISO/IEC 14443 for Type B Proximity Contactless Identification Cards", retrieved from https://www.digchip.com/application-notes/22/15746.php, Nov. 2005, pp. 1-28.

Anonymous, "EPC™ Radio-Frequency Identity Protocols Class-1 Generation-2 UHF RFID Protocol for Communications at 860 MHz-960 MHz Version 1.0.9", Specification for RFID Air Interface, EPCglobal Inc™, Jan. 2005, pp. 1-94.

Boettcher, Lars et al., "Embedding of Chips for System in Package realization—Technology and Applications", 2008 3rd International Microsystems, Packaging, Assembly & Circuits Technology Conference; Taipei, Taiwan, 2008, 4 pages.

Fernandez-Carames, et al., "A Review on Human-Centered IoT—Connected Smart Labels for the Industry 4.0", Journals & Magazines, IEEE, vol. 6, May 7, 2018, pp. 25939-25957.

ISO/IEC, "Cards and Security Devices for Personal Identification—Contactless Vicinity Objects—Part 1: Physical Characteristics", ISO/IEC 15693-1, International Organization for Standardization, 3rd Edition, Jul. 5, 2018, 9 pages.

Kuhnapfel, U et al., "Endoscopic surgery training using virtual reality and deformable tissue simulation, Computers & Graphics", vol. 24, issue 5, 2000, 671-682.

(56) References Cited

OTHER PUBLICATIONS

Jambaulikar, et al., "Electronic Paper Displays in Hospital Operations: Proposal for Deployment and Implementation", JMIR Form Res 2021, vol. 5, iss. 8, e30862, 2021, pp. 1-11.

* cited by examiner 10
14
12
20
13
316
A
2!
bc
136
22
15
18
13A
13B
13C 100
110
Assembly
102A
120
Warehouse
102B
130
Transit
102C
140
Customs
102D
150
Distribution
102E
160
Local transit
102F
170
Hospital
102G
180
O.Rs
102H
50
HUB

Figure 4:
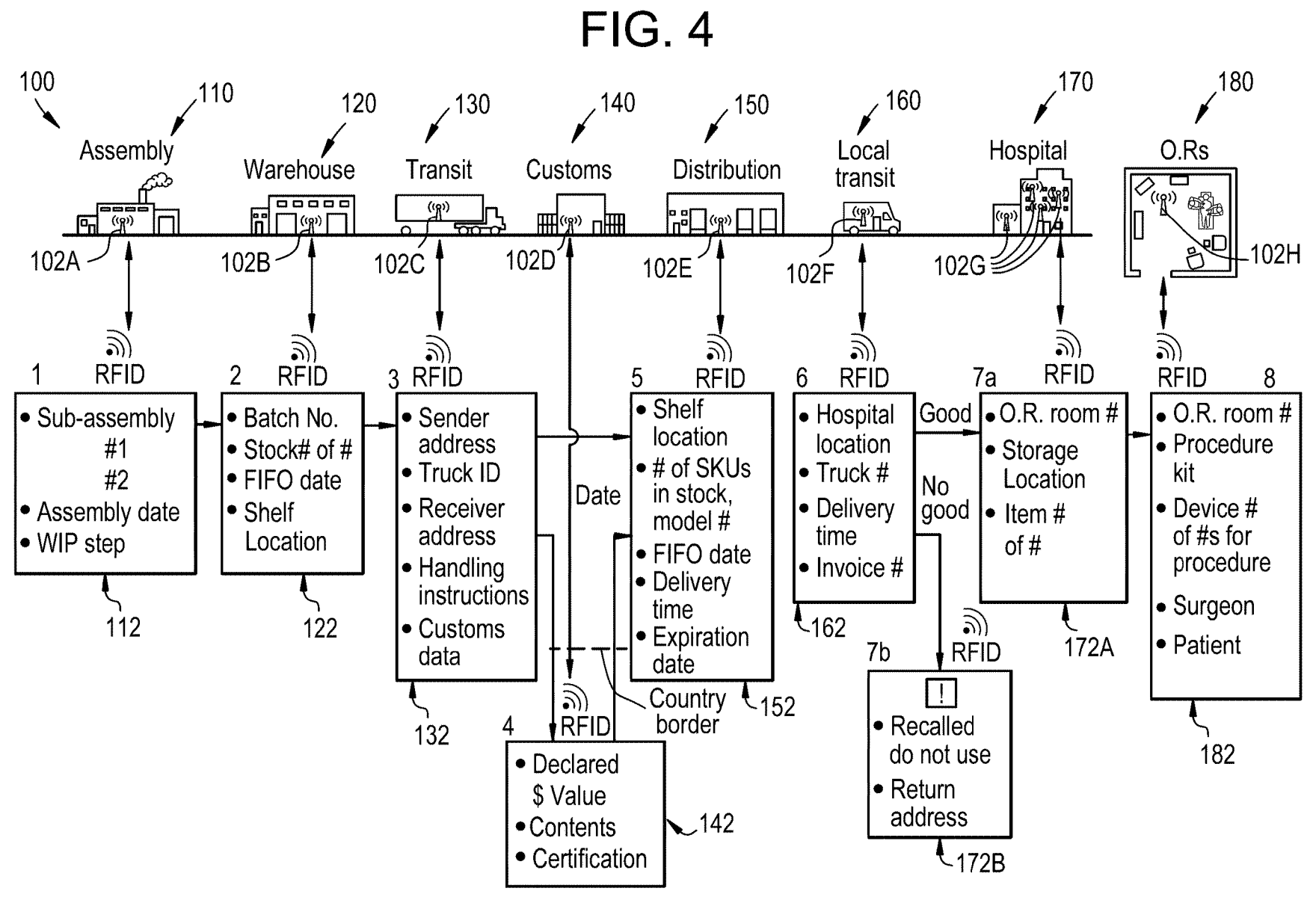

110 Assembly 102A RFID
1
- Sub-assembly #1 #2
- Assembly date
- WIP step
112

120 Warehouse 102B RFID
2
- Batch No.
- Stock# of #
- FIFO date
- Shelf Location
122

130 Transit 102C RFID
3
- Sender address
- Truck ID
- Receiver address
- Handling instructions
- Customs data
132

140 Customs 102D RFID
4
- Declared $ Value
- Contents
- Certification
142

Date

Country border

150 Distribution 102E RFID
5
- Shelf location
- # of SKUs in stock, model #
- FIFO date
- Delivery time
- Expiration date
152

160 Local transit 102F RFID
6
- Hospital location
- Truck #
- Delivery time
- Invoice #
162

Good

No good

170 Hospital 102G RFID
7a
- O.R. room #
- Storage Location
- Item # of #
172A

RFID
7b
!
- Recalled do not use
- Return address
172B

180 O.Rs 102H RFID
8
- O.R. room #
- Procedure kit
- Device # of #s for procedure
- Surgeon
- Patient
182

1090

Life of Transducer

Phase margin shift due to exposure to increased temperatures

Phase margin

Time

SYSTEMS AND METHODS FOR STORAGE AND TRANSFER OF SMART PACKAGING METADATA

CROSS-REFERENCE TO RELATED APPLICATION

This application claims the benefit of and priority to U.S. Provisional Application No. 63/525,572, filed Jul. 7, 2023, the contents of which is herein incorporated by reference in its entirety.

FIELD

The present disclosure relates generally to smart surgical devices, systems, and methods.

BACKGROUND

Surgical instruments are manufactured to meet specific performance metrics in order to ultimately perform a surgical procedure in a safe and effective manner. Following manufacture, surgical instruments are shipped all over the world to hospitals and surgical centers, and along the supply chain, the surgical instruments are handled by a variety of persons, including transit operators, warehouse operators, customs officials, hospital staff, surgical teams, and more.

While safe and effective performance of the surgical instrument is the goal, problems can arise. In some cases, problems with the surgical instrument may arise due to manufacturing issues. In other cases, problems may arise as a result of mishandling during transit, such as improper storage techniques or extreme environmental phenomena. In still other cases, problems may arise as a result of incompatibility with other surgical equipment or improper usage in an operating room during a surgical procedure.

Accordingly, there remains a need for improved systems and methods.

SUMMARY

In an embodiment, systems are provided that include a manufacturer-sealed sterile surgical packaging containing a surgical instrument configured to be used in a surgical procedure, a graphical display, at least one data processor in operable communication with the graphical display, and memory in operable communication with the at least one data processor, and storing instructions configured to cause the at least one data processor to perform operations. The operations can include storing parameters corresponding to the surgical instrument, receiving a data set characterizing parameters associated with the surgical instrument, adjusting based on the received data, the catalogued parameters, determining a graphical depiction characterizing the adjusted parameters, and providing the graphical depiction of the adjusted parameters on the graphical display.

The system can vary in a number of ways. For example, the cataloged parameters and adjusted parameters include information characterizing at least one of historic states, future states, and operational information. In other aspects, the historic states can include at least one of manufacturing information, materials and components information, geographical origin information, and environmental information experienced by the surgical packaging. In other embodiments, the future states can include at least one of an intended destination information, environmental requirements information, customs information, disposal information, and error reporting procedures information. In other aspects, the operational information can include at least one of product compatibility information, expected lifecycle information, and operational instructions. In some variations, the operations can further comprise providing, based on an on-demand user request, at least a portion of the catalogued parameters. In other embodiments, the on-demand user request can require an authentication to access the catalogued parameters. In some variations, the graphical display can include at least one e-ink label. In some embodiments, the adjusted parameters can be transmitted and displayed on a remote device in electronic communication with the manufacturer-sealed sterile surgical packaging.

In another embodiment, a method is provided including storing parameters corresponding to a surgical instrument, the surgical instrument contained within a manufacturer-sealed sterile surgical packaging, the manufacturer-sealed sterile surgical packaging including a display disposed thereon, receiving, a data set characterizing parameters associated with the surgical instrument, adjusting, based on the received data, the stored parameters, determining a graphical depiction characterizing the adjusted parameters, and providing the graphical depiction of the adjusted parameters on the display.

The method can vary in a number of ways. For example, the cataloged parameters and adjusted parameters can include information characterizing at least one of historic states, future states, and operational information. In other aspects, the historic states can include at least one of manufacturing information, materials and components information, geographical origin information, and environmental information experienced by the surgical packaging. In other embodiments, the future states can include at least one of an intended destination information, environmental requirements information, customs information, disposal information, and error reporting procedures information. In other aspects, the operational information can include at least one of product compatibility information, expected lifecycle information, and operational instructions. In some variations, the method can include providing, based on an on-demand user request, at least a portion of the cataloged parameters. In other embodiments, the on-demand user request can be authenticated prior to providing the at least a portion of the cataloged parameters. In some variations, the at least one display can include at least one e-ink label.

Non-transitory computer program products are also provided. In one embodiment, a non-transitory computer program product is provided and can store instructions which, when executed by at least one data processor forming part of at least one computing system, cause the at least one data processor to implement operations including storing parameters corresponding to a surgical instrument, the surgical instrument contained within a manufacturer-sealed sterile surgical packaging, the manufacturer-sealed sterile surgical packaging including a display disposed thereon, receiving, a data set characterizing parameters associated with the surgical instrument, adjusting, based on the received data, the catalogued parameters, determining a graphical depiction characterizing the adjusted parameters, and providing the graphical depiction of the adjusted parameters on the display.

In an embodiment, systems are provided that include a manufacturer-sealed sterile surgical packaging containing a surgical instrument configured to be used in a surgical procedure, a graphical display, at least one data processor in operable communication with the graphical display, and memory in operable communication with the at least one data processor, and storing instructions configured to cause the at least one data processor to perform operations. The operations can include recording historical data points of the surgical instrument, determining a degradation level of the surgical instrument based on the historical data point, determining an altered set of operating parameters based on the degradation level of the surgical instrument, and providing the altered set of operating parameters.

The system can vary in a number of ways. For example, the recording of historical data points can include tracking the amount of sterilization procedures the surgical instrument has underwent. In some variations, the recording of historical data points can include tracking the amount of operations performed by the surgical instrument. In other variations, the recording of historical data points can include tracking the environmental conditions where the surgical instrument is located. In some variations, the altered set of operating parameters can increase an operational accuracy of the surgical instrument. In some aspects, the altered operating parameters can be transmitted and displayed on a remote device in electronic communication with the manufacturer-sealed sterile surgical packaging.

In another embodiment, a method is provided and can include recording historical data points of a surgical instrument contained within a manufacturer-sealed sterile surgical packaging, the surgical instrument configured to be used in a surgical procedure, determining a degradation level of the surgical instrument based on the historical data points, determining an altered set of operating parameters based on the degradation level of the surgical instrument, and providing the altered set of operating parameters.

The method can vary in a number of ways. For example, the recording of historical data points can further include tracking an amount of sterilization procedures applied to the surgical instrument. In some variations, the recording of historical data points can further include tracking an amount of operations performed by the surgical instrument. In some aspects, the recording of historical data points can further include tracking environmental conditions where the surgical instrument is located. In some variations, the altered set of operating parameters can increase an operational accuracy of the surgical instrument. In other aspects, the altered operating parameters can be transmitted and displayed on a remote device in electronic communication with the manufacturer-sealed sterile surgical packaging.

In another embodiment, a non-transitory computer program product is provided. The non-transitory computer program product can store instructions that, when executed by at least one data processor forming part of at least one computing system, cause the at least one data processor to implement operations. The operations can include recording historical data points of the surgical instrument, determining a degradation level of the surgical instrument based on the historical data points, determining an altered set of operating parameters based on the degradation level of the surgical instrument, and providing the altered set of operating parameters.

The non-transitory computer program product can vary in a number of ways. For example, the recording of historical data points can include tracking an amount of sterilization procedures the surgical instrument has underwent. In some embodiments, the recording of historical data points can include tracking an amount of operations performed by the surgical instrument. In some aspects, the recording of historical data points can include tracking environmental conditions where the surgical instrument is located. In some aspects, the altered operating parameters can be transmitted and displayed on a remote device in electronic communication with the manufacturer-sealed sterile surgical packaging.

In an embodiment, systems are provided that include a manufacturer-sealed, sterile surgical packaging, a surgical instrument stored within the manufacturer-sealed, sterile packaging, a first transceiver contained within the manufacturer-sealed, sterile surgical packaging and configured to transmit a first data set including a first amount of data, a second transceiver contained within the manufacturer-sealed, sterile surgical packaging and configured to transmit a second data set including a second amount of data, the second amount of data greater than the first amount of data, and a power supply contained within the manufacturer-sealed and connected to the second transceiver, wherein the second transceiver is intermittently powered by the power supply.

The systems can vary in a number of ways. For example, the second transceiver can be non-active while the first transceiver is active. In some embodiments, the second transceiver can be constantly powered by the power supply. In some aspects, the second transceiver can be configured to record historical data points. In some variations, the first transceiver can be non-activate while the second transceiver is activate. In other variations, the first transceiver can be at least one RFID chip embedded within the manufacturer-sealed, sterile surgical packaging. In some embodiments, the second transceiver can include at least one data processor disposed in the surgical packaging, and memory disposed in the surgical packaging storing instructions configured to cause the at least one data processor to perform operations can include to record historical data points of the surgical instrument provided to the second transceiver via at least one sensor disposed in the surgical packaging. In some variations, a switch can be positioned between the power source and the second transceiver to selectively activate the second transceiver. In some embodiments, the surgical instrument can be positioned within a first compartment within the manufacturer-sealed, sterile surgical packaging, and the power source is positioned within a second compartment within the manufacturer-sealed, sterile surgical packaging, separate from the first compartment.

In another embodiment, a method is provided and can include activating a first transceiver contained within a manufacturer-sealed, sterile surgical packaging, the manufacturer-sealed, sterile surgical packaging containing a surgical instrument stored therein, transmitting a first data set from the first transceiver, wherein the first set of data includes a first amount of data, activating a second transceiver contained within the manufacturer-sealed, sterile surgical packaging by connecting the second transceiver to a power supply contained within the manufacturer-sealed, sterile surgical packaging, powering the second transceiver intermediately via the power supply, and transmitting a second data set from the second transceiver, wherein the second set of data includes a second amount of data, the second amount of data greater than the first amount of data.

The method can vary in a number of ways. For example, the method can include deactivating the first transceiver prior to activating the second transceiver. In some embodiments, the method can include deactivating the second transceiver prior to activating the first transceiver. The first transceiver can be at least one RFID chip embedded within the manufacturer-sealed, sterile surgical packaging. The method can also include recording historical data points of the surgical instrument provided to the second transceiver via at least one sensor disposed in the surgical packaging. In some variations, the method can include adjusting operating parameters transmitted by the second transceiver based on the recorded historical data points. In some aspects, the method can include constantly powering the second transceiver via the power supply. In some embodiments, the method can include actuating a switch positioned between the power source and the second transceiver to selectively activate the second transceiver. In some variations, the surgical instrument can be positioned within a first compartment within the manufacturer-sealed, sterile surgical packaging, and the power source is positioned within a second compartment within the manufacturer-sealed, sterile surgical packaging, separate from the first compartment.

In an embodiment, systems are provided that include a manufacturer-sealed sterile surgical packaging containing a surgical instrument, a graphical display disposed on the manufacturer-sealed sterile surgical packaging, a data processor disposed in the surgical packaging, and memory in operable communication with the data processor, the memory storing instructions configured to cause the at least one data processor to perform operations. The operations include storing a plurality of display information sets corresponding to the surgical instrument, receiving a data set including a stage along a supply chain progression, determining, based on the received location along the supply-chain progression, a graphical depiction characterizing at least one of the plurality of stored display information sets, and providing the graphical depiction of the determined at least one display information set on the graphical display.

The system can vary in a number of ways. For example, in some embodiments, the at least one display can include at least one e-ink label. In some variations, the plurality of display information sets can include information characterizing at least one of manufacturing states, transit states, and operational information. In some variations, the manufacturing states can include at least one of manufacturing information, materials and components information, and geographical storage information. In other embodiments, the transit states can include at least one of an intended destination information, handling information, and customs information. In some embodiments, the operational information can include at least one of intended destination information, intended user information, and operational instructions. In some aspects, a power supply can be contained within the manufacturer-sealed sterile surgical packaging, and configured to power the display. In some embodiments, the operations can include to receive data characterizing a stage of the supply-chain progression of the system, to determine a corresponding display information set from the plurality of display information sets, and providing the determined display information set via the display. In some variations, at least one of the display information sets can include a scanable code. In some embodiments, the received data set can include environmental parameters the manufacturer-sealed sterile surgical packaging is present within. In some variations, the graphical depiction on the graphical display can be adjusted when the manufacturer-sealed sterile surgical packaging passes to a second stage along the supply-chain progression.

In another embodiment, a method is provided that includes storing a plurality of display information sets corresponding to a surgical instrument, the surgical instrument contained within a manufacturer-sealed sterile surgical packaging, the manufacturer-sealed sterile surgical packaging including a graphical display disposed thereon, receiving a data set including a stage along a supply chain progression, determining, based on the received location along the supply-chain progression, a graphical depiction characterizing at least one of the plurality of stored display information sets, and providing the graphical depiction of the determined at least one display information set on the graphical display.

The method can vary in a number of ways. For example, the at least one display can include at least one e-ink label. In some variations, the plurality of display information sets can include information characterizing at least one of manufacturing states, transit states, and operational information. In some variations, the manufacturing states can include at least one of manufacturing information, materials and components information, and geographical storage information. In other embodiments, the transit states can include at least one of an intended destination information, handling information, and customs information. In some embodiments, the operational information can include at least one of intended destination information, intended user information, and operational instructions. In some variations, a power supply can be contained within the manufacturer-sealed sterile surgical packaging, and configured to power the display. In some embodiments, the method can include receiving data characterizing a stage of the supply-chain progression of the system, determining a corresponding display information set from the plurality of display information sets, and providing the determined display information set via the display. In some variations, at least one of the display information sets can include a scanable code. In some embodiments, the graphical depiction on the graphical display can be adjusted when the manufacturer-sealed sterile surgical packaging passes to a second stage along the supply-chain progression.

In another embodiment, a non-transitory computer program product is provided. The non-transitory computer program product can store instructions that, when executed by at least one data processor forming part of at least one computing system, cause the at least one data processor to implement operations. The operations can include storing a plurality of display information sets corresponding to a surgical instrument, the surgical instrument contained within a manufacturer-sealed sterile surgical packaging, the manufacturer-sealed sterile surgical packaging including a graphical display disposed thereon, receiving a data set including a stage along a supply chain progression, determining, based on the received location along the supply-chain progression, a graphical depiction characterizing at least one of the plurality of stored display information sets, providing the graphical depiction of the determined at least one display information set on the graphical display.

In an embodiment, systems are provided that include at least one primary packaging, at least one graphical display disposed on the primary packaging, and an electronic management system in electronic communication with the primary packaging. The electronic management system is configured to receive data characterizing a list of compatible secondary packagings stored on the primary packaging, determine a compatible secondary packaging in electronic communication with the electronic management system from the list of compatible secondary packagings stored on the primary packaging, and provide data characterizing the determined compatible secondary packaging on the at least one graphical display of the primary packaging.

The system can vary in a number of ways. For example, the compatible secondary packaging is determined based on a surgical procedure the primary packaging can be configured to be used therein. In some variations, the determined compatible secondary packaging can be provided on the at least one display of the primary packaging. In some aspects, the at least one display can include at least one e-ink label.

In other embodiments, the compatible secondary packaging can include a second display disposed on the compatible secondary packaging. In some variations, the electronic management system can be further configured to receive data characterizing a list of compatible primary packagings stored on the secondary packaging, determine a compatible primary packaging in electronic communication with the electronic management system from a list of compatible primary packagings stored on the secondary packaging, and provide data characterizing the determined compatible primary packaging on the second graphical display of the secondary packaging. In some embodiments, the determined compatible primary packaging can be provided on the second display of the secondary packaging. In other embodiments, the electronic management system can be further configured to provide, based on the determined compatible secondary packaging, operational information for the primary packaging and compatible secondary packaging. In some aspects, the operational information can include at least one of product compatibility information and operational instructions.

In another embodiment, a method is provided. The method can include receiving data characterizing a list of compatible secondary packagings stored on a primary packaging in electronic communication with an electronic management system, determining a compatible secondary packaging in electronic communication with the electronic management system from the list of compatible secondary packagings stored on the primary packaging, and providing data characterizing the determined compatible secondary packaging on an at least one graphical display of the primary packaging.

The method can vary in a number of ways. For example, For example, the compatible secondary packaging is determined based on a surgical procedure the primary packaging can be configured to be used therein. In some variations, the determined compatible secondary packaging can be provided on the at least one display of the primary packaging. In some aspects, the at least one display can include at least one e-ink label. In other embodiments, the compatible secondary packaging can include a second display disposed on the compatible secondary packaging. In some embodiments, the method can further include receiving data characterizing a list of compatible primary packagings stored on the secondary packaging, determining a compatible primary packaging in electronic communication with the electronic management system from a list of compatible primary packagings stored on the secondary packaging, and providing data characterizing the determined compatible primary packaging on the second graphical display of the secondary packaging. In further aspects, the determined compatible primary packaging can be provided on the second display of the secondary packaging. In some embodiments, the method can further include providing, based on the determined compatible secondary packaging, operational information for the primary packaging and compatible secondary packaging. In some aspects, the operational information can include at least one of product compatibility information and operational instructions.

In another embodiment, a non-transitory computer program product is provided. The non-transitory computer program product can store instructions which, when executed by at least one data processor forming part of at least one computing system, cause the at least one data processor to implement operations. The operations can include receiving data characterizing a list of compatible secondary packagings stored on a primary packaging in electronic communication with an electronic management system, determining a compatible secondary packaging in electronic communication with the electronic management system from the list of compatible secondary packagings stored on the primary packaging, and providing data characterizing the determined compatible secondary packaging on an at least one graphical display of the primary packaging.

BRIEF DESCRIPTION OF DRAWINGS

The present invention is described by way of reference to the accompanying figures which are as follows:

FIG. 1 is a top view of a passive RFID tag, according to an embodiment;

FIG. 4 is a diagram of a supply chain for a smart packaging system including a surgical instrument, and the kinds of information exchanged to and from the smart packaging system at various points along the supply chain, according to an embodiment;

DETAILED DESCRIPTION

Figure 2:
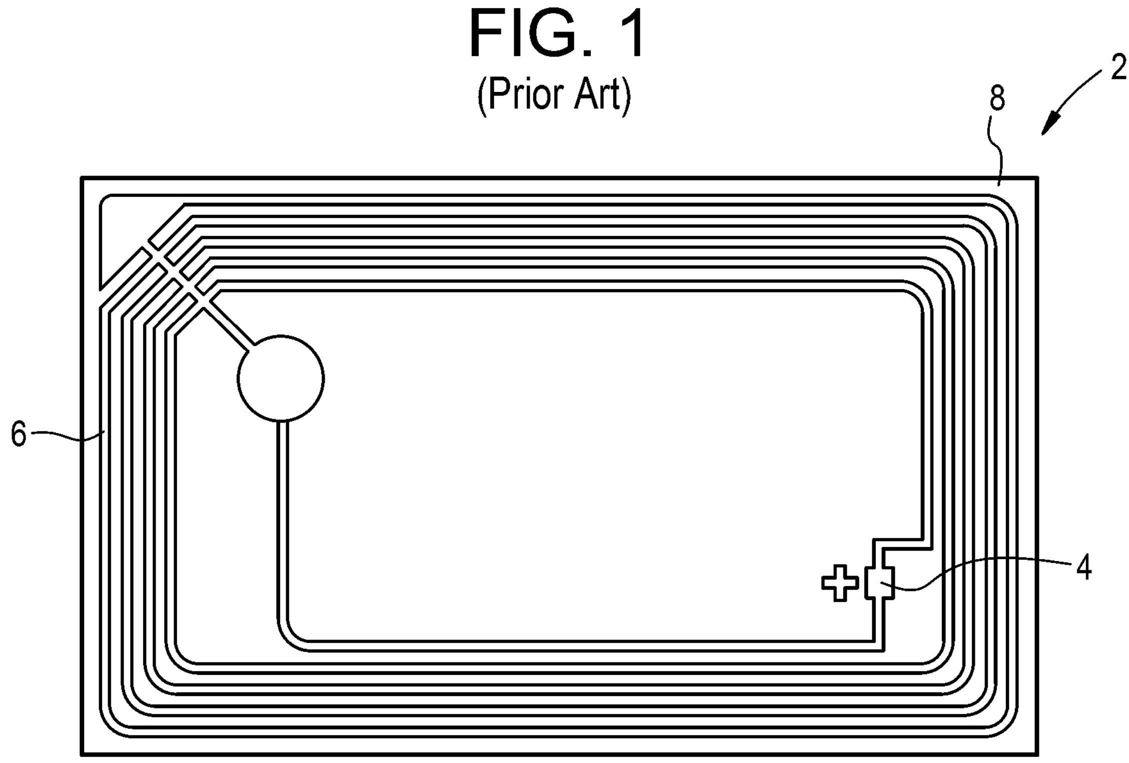
FIG. 2 is a side schematic view of a smart packaging system containing a surgical instrument according to an embodiment.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Smart surgical devices, systems, and methods are provided. The use of smart devices, systems, and methods can generally enable the storing, sharing, and utilization of information throughout a supply chain, as well as to assist in the management of various systems, procedures, and aspects of healthcare facilities in which they are used. At all times, information directed to aspects of the supply chain and of healthcare facilities can be logged, monitored, and reviewed in order to adjust facets of the supply chain and/or healthcare facilities in real time. Additionally, analysis of the compiled information can be used in order to minimize or avoid pitfalls and issues associated with the supply chain and/or products flowing through the supply chain, as well as to minimize or avoid pitfalls and issues associated with the coordination of surgical procedures and associated devices at healthcare facilities. Overall, smart devices, systems, and methods can improve the efficiency of the supply chain through the management of information associated with products flowing through that supply chain, and they can improve the efficiency of the healthcare facilities in which they are deployed for use in surgical procedures. While the specific types of smart devices, systems, and methods can vary, in some aspects the packaging of the products themselves can be leveraged in order to consistently track, monitor, and record information associated with the products. Further, tracking devices (e.g., scanners, beacons, etc.) and/or a centralized computer management system can be employed as part of the smart systems and devices.

The use of smart devices, systems, and methods can also impact the operations of a healthcare provider, such as during a surgery involving the smart surgical devices. Information can be recorded, stored, monitored, and acted upon before, during, and after a surgical procedure involving the smart surgical device in order to improve the performance and to minimize the operational risks of the smart surgical device and of future smart surgical devices.

Smart devices, including smart packaging systems, can act on the information they receive to provide recommendations, warnings, guidelines, and other information to various personnel associated with healthcare facilities. This provided information can contemplate all aspects of daily procedures at healthcare facilities, including scheduling, logistics, coordination of surgical procedures, recommended handling instructions during specific surgical procedures, and more. Moreover, the smart devices and smart packaging systems themselves can be designed to include various physical aspects intended to assist personnel in acting upon the provided information.

As indicated above, in some aspects the smart devices, systems, and methods can utilize smart packaging systems, which can be included on an outer packaging containing one or more surgical instruments. In an exemplary embodiment, the outer packaging can include a power source, one or more radio frequency identification ("RFID") tags, and one or more sensors capable of measuring environmental aspects. The one or more RFID tags can take on various forms and may generally include passive and active RFID tags. Passive RFID tags can include an RFID chip (or integrated circuit, "IC"), an antenna, and a substrate. The IC contains a logical control unit, memory, and transceiver, which can be used for decoding, decrypting, and error checking. The antenna is used to receive/transmit information, such as electronic data, to and from an external electronic system with its own reception and/or transmission capabilities (e.g., a reader). The substrate holds the chip and antenna together and provides the RFID tag with structure. Passive RFID tags can receive power in the form of electromagnetic energy (e.g., radio energy) transmitted by a reader and received by the antenna of the passive RFID tag. An example of a passive RFID tag 30 can be seen in FIG. 1. The passive RFID tag 2 includes an IC 4 electronically coupled to an antenna 6. The IC 4 and the antenna 6 are mounted on a substrate 8.

Active RFID tags may include components similar to those of passive RFID tags with the addition of a separate power source (e.g., an integrated battery). Further, in some variations, other kinds of sensors or chips, such as near field communication (NFC) sensors, may be used in addition to, or in place of, the one or more RFID tags.

In some variations, the outer packaging can include additional memory storage and/or one or more additional processors in electronic communication with the one or more RFID tags in order to increase the capabilities of the RFID tags. The smart packaging system can also include one or more of a display, such as an e-ink display, LCD display, touchscreen, or equivalent, and/or a readable medium, such as a barcode, QR code, or equivalent. In some variations, the smart packaging system can include data ports, such as USB-type ports. With some or all of these features, the smart packaging system can generally be capable of taking in data from external sources, such as computers, computer networks, and data received from its one or more sensors, and the smart packaging system can generally be capable of transmitting data and/or presenting information to computers, computer networks, users, scanning devices, RFID readers, and any device capable of receiving data from features of the smart packaging system.

The surgical instrument(s) and/or surgical components contained within the outer packaging can vary in both form and function. In some variations, the entire surgical instrument can be a "smart" instrument in which the status and operations of the surgical instrument can be monitored, recorded, and altered at any time. For example, if the surgical instrument is an endo-cutter configured to incise and staple tissue, an amount of torque applied by the jaws of the instrument can be monitored throughout a surgical procedure. If it is determined by the HUB that too much torque is being applied by a surgeon, a maximum torque limit can be imposed wirelessly on the instrument in real time so as to prevent the occurrence of an accident. Further, with such surgical instruments, if, during an operation involving the instrument, an accident does occur, details surrounding the accident can be recorded and stored either within the memory of the packaging or virtually on the HUB. This information can then be used to determine the source of the accident, and, for example, whether a recall should be issued for similarly-situated surgical instruments.

In other variations, sub-portions of the surgical instrument can be "smart," while other portions of the instrument may be electronically isolated from the "smart" sub-portions such that the status and operations of the surgical instrument are not capable of being monitored, recorded, or altered whatsoever. For example, in the same endo-cutter described above, a jaw-driver sub-system may be "smart," but a sub-system concerning articulation of a shaft of the endo-cutter may not be "smart." Even though the shaft may be electronically articulable, it may not be in electronic communication with the HUB and/or the outer packaging, and it, accordingly, may be "hidden" from monitoring. These examples are exemplary only, and more concrete examples and variations are described below.

An example of a smart packaging system 10 is depicted in FIG. 2. The illustrated smart packaging system 10 includes a packaging 12 containing a surgical instrument 14 therein. The surgical instrument 14 can be any surgical instrument or surgical material, such as an endocutter as shown. The smart packaging system 10 can include a controller 13 that is configured to execute functions of the smart packaging system 10. The controller 13 can generally include a control unit 13A, a logic unit 13B, and a memory 13C that enable functionality of the controller 13. The smart packaging system 10 can also include an internal power source 15, such as a battery, that is capable of providing power to various components of the smart packaging system 10, including the controller 13, described herein. The packaging 12 can also include an RFID tag 16 configured to transmit and receive information from an external source. A serial number 18, which may or may not feature encrypted data, can be locating on the packaging 12 such that it can be read by a handler or a computer system. The packaging 12 can further include a scanable or readable medium 20, such as a QR code or a barcode and a display 22, such as the kind mentioned previously (e.g., an e-Ink display). While not shown, the smart packaging system 10 can contain additional surgical accessories, components, and elements that may be disposed in a compartment separate from the surgical instrument 14. The surgical accessories, components, and elements can be used in conjunction with or separate from the surgical instrument 14. Together, these items can generally be referred to as the contents of the smart packaging system 10. For example, the surgical instrument 14 can be a surgical stapler, and the contents of the smart packaging system 10 can include staple cartridges that are compatible with the surgical stapler, which may be packaged within the smart packaging system 10 separate from the surgical stapler, such as in a sub-compartment of the packaging 12. Reference will be made to the smart packaging system 10 and its component parts for exemplary purposes only.

The smart packaging system 10 can receive and present information relevant to personnel who may interact with the smart packaging system 10 along the life cycle of the contained surgical instrument 14, as well as with other surgical instruments and products that interface with the contained surgical instrument 14. The kind of personnel and the relevance of the information will vary depending on where the surgical instrument 14 and the smart packaging system 10 are in their lifecycle. Following manufacture in a factory, the surgical instrument 14 will be packaged and prepared for delivery to eventually end up at a healthcare facility, such as a hospital or surgery center, to be used in a surgical procedure. To arrive at that the hospital or surgery center, the smart packaging system 10 will undergo a series of interactions with various personnel, including factory personnel, warehouse personnel, transit personnel, customs personnel, and hospital personnel. At each phase of its journey, the smart packaging system 10 can receive and transmit relevant information to personnel. Although the smart packaging system 10 can store a variety of information, the smart packaging system 10 can, based on context, selectively provide only relevant information.

Additionally, on its journey, the smart packaging system 10 may communicate with a central network, also called a HUB 50, which can monitor and coordinate information including and about the smart packaging system 10. The HUB 50 can be present along the smart packaging supply chain in the form of beacons 102 placed in key locations, such as a hospital operating room (OR). When a beacon 102 or other facet of the HUB 50 detects that the smart packaging system 10 is in close proximity, information can be exchanged between the smart packaging system 10 and the HUB 50, and information can be exchanged between the HUB 50 and various external networks.

Each beacon 102 can include a transceiver, a transponder, a power source, a processor, and a local memory. The beacons 102, generally can operate as an RFID reader in electronic communication with a central network, HUB 50. The beacons 102 can be in wired communication or in wireless communication, such as via infrared communication, radio communication, Wi-Fi communication, Bluetooth, etc. The RFID reader can be a passive reader that can receive signals transmitted by an active RFID tag, the RFID reader can be an active reader that can transmit interrogator signals and receive replies, such as authentication replies, from an RFID tag. During operation, the beacons 102 can receive transmitted data from the smart packaging system 10 characterizing information recorded by the smart packaging system 10 related it its experiences since manufacture. The beacons 102 can then transmit that received data to the HUB 50 where it can be stored, analyzed, and/or acted upon. The beacons 102 can also transmit information from the HUB 50 to a nearby smart packaging system 10.

Figure 3A:
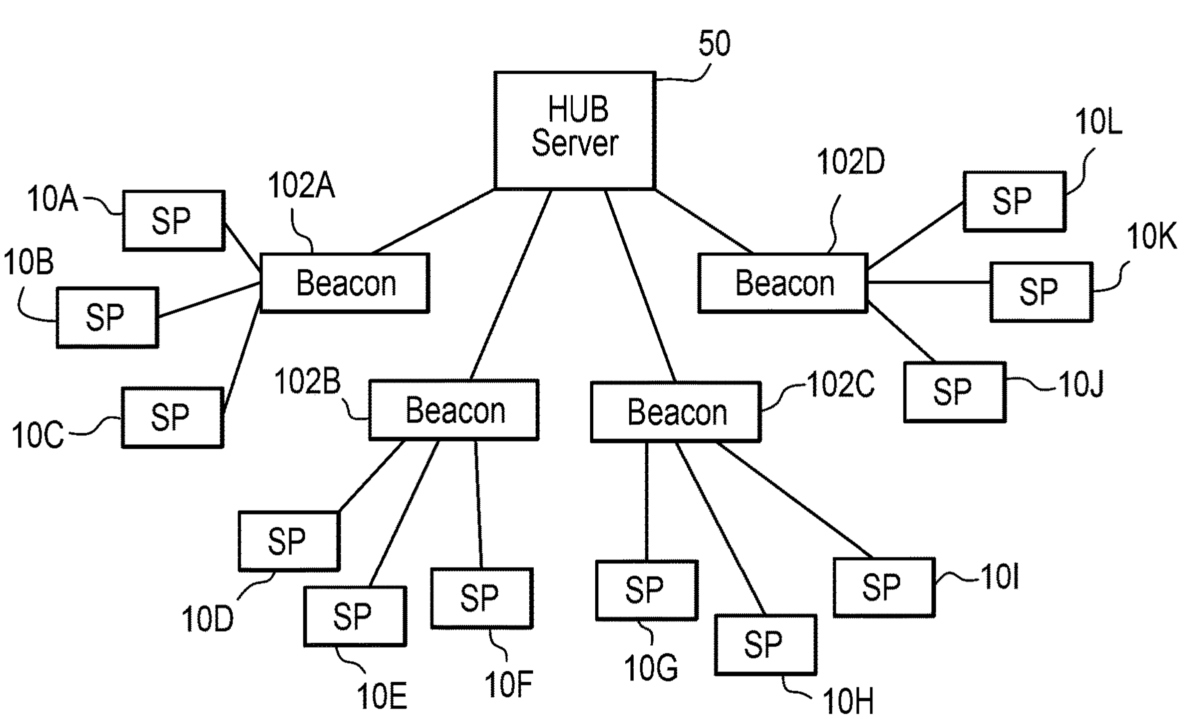
FIG. 3A is a diagram of a smart packaging system in electronic communication with a beacon and a HUB in an operating room, according to an embodiment.
Figure 3B:
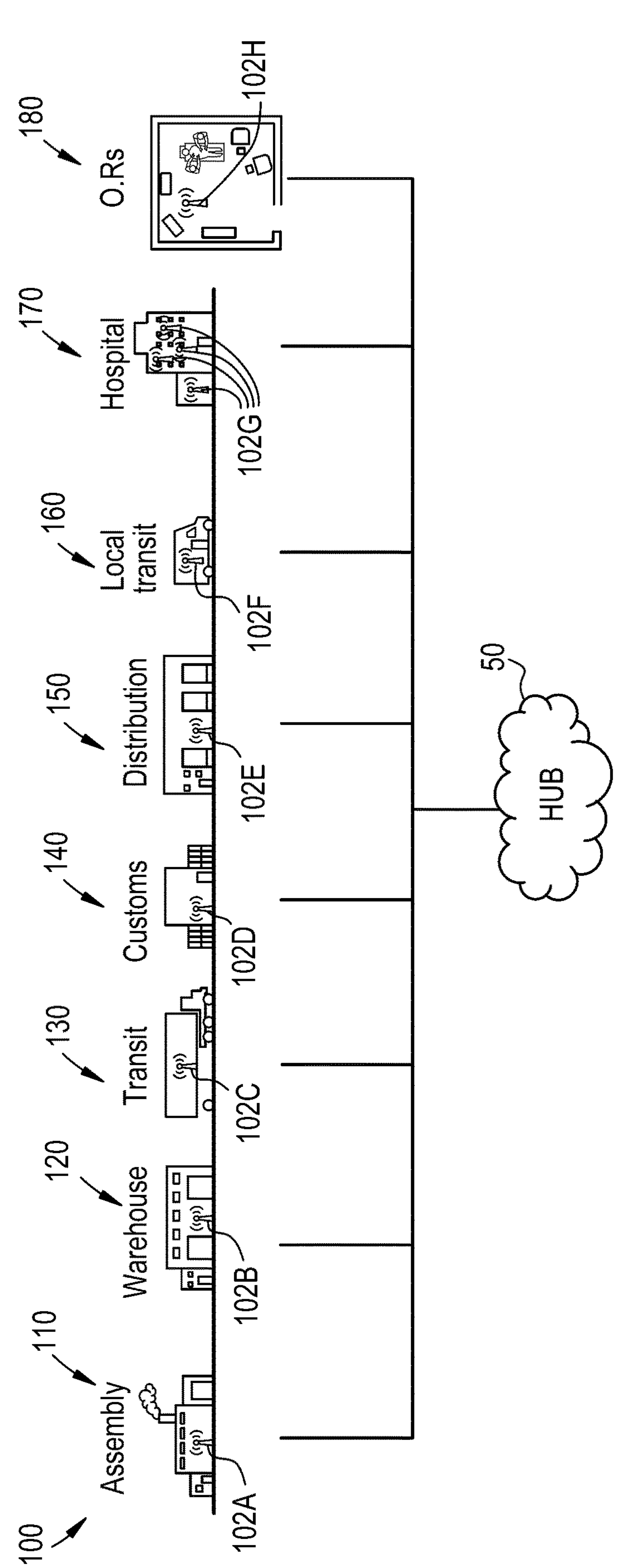
FIG. 3B is a diagram of a supply chain for a smart packaging system, according to an embodiment.

A non-limiting example of the exchange of information between the beacon 102 (or HUB 50, generally) and the smart packaging system 10 is shown in FIG. 3A and FIG. 3B In FIG. 3A, a chart is depicted that shows a general hierarchy structure between the HUB 50, the beacons 102 (individually represented as beacons 102A-102D), and the smart packaging system 10 or systems 10 (individually represented as smart packaging systems 10A-10L). The HUB 50 can be in communication with the beacons 102, which can be in communication with the smart packaging systems 10. In some variations, however, the smart packaging system 10 can transmit information directly to the HUB 50 and receive information directly from the HUB 50 using its own transmission and reception capabilities. In FIG. 3B, a chart is depicted showing an exemplary supply chain 100, and different contexts in which the smart packaging system 10 may communicate with the HUB 50 via one or more beacons 102. The interplay between the smart packaging systems 10 and the HUB 50, via the beacons 102, can be important depending upon the context in which the smart packaging system 10 is located. This context can change as the smart packaging system 10 moves from manufacture to transit to use through a supply chain.

The supply chain 100 shown in FIG. 3B and in FIG. 4 is shown with simplified versions of key stages along the supply chain of a surgical device or system, making the depiction of the supply chain 100 illustrative and exemplary, rather than mandatory and necessary. In reality, actual supply chains may include these stages in a different order, or they may include additional stages, duplicate certain stages, or omit stages altogether.

The first depicted stage in the supply chain 100 is the assembly stage 120, which can include a beacon 102A to facilitate communication with the HUB 50. The assembly stage 120 represents manufacture of the surgical instrument 14. Information exchanged at the assembly stage 120 can include assembly information 112 pertaining to the surgical instrument 14 itself, including its performance metrics, manufacture specifications, tolerances, safety and usage information, etc. The assembly information 112 can also include, for example, sub-assembly information pertaining to one or more sub-assemblies that are compatible with the surgical instrument. Additionally, the assembly information 112 can include work-in-progress (WIP) step and assembly date of the surgical instrument.

The second depicted stage in the supply chain 100 is the warehouse stage 110, which can include a beacon 102B. The warehouse stage 110 represents storage of the smart packaging system 10 prior to shipment thereof. Information exchanged at the warehouse stage 110 can include warehouse information 122, such as batch number, stock number and count, FIFO date, and shelf location so that the smart packaging system 10 can be tracked and located within the warehouse itself.

The third depicted stage in the supply chain 100 is the transit stage 130, which can include a beacon 102C. The transit stage 130 represents transit of the smart packaging system 10 from the warehouse to end up at a distribution center. Information exchanged at the transit stage 130 can include transit information 132, such as sender address, truck ID, receiver address, handling instructions, and customs data.

After the third depicted stage, the smart packaging system 10 may optionally be shipped across geopolitical borders, including to international locations, before ending up at a distribution center. The fourth depicted stage is the customs stage 140, which can include a beacon 102D, and it represents those occurrences when the smart packaging system 10 must cross a geopolitical border. Information exchanged at the customs stage can include customs information 142, such as declared value, contents, and certification.

If the smart packaging system 10 is not be shipped internationally, the smart packaging system can proceed from the transit stage 130 directly to the distribution stage 150. If the smart packaging system 10 is shipped internationally, it can proceed to the distribution stage 150 following the customs stage 140. The distribution stage 150 represents a warehouse or distribution center, which can include a beacon 102E that receives the smart packaging system before it is sent to its ultimate destination, such as a hospital. Information exchanged at the distribution stage 150 can include distribution information 152, such as shelf location, number of specific stock keeping units (SKUs) in stock, model number, FIFO date, delivery time, and expiration date.

The sixth depicted stage in the supply chain 100 is the local transit stage 160, which can include a beacon 102F. The local transit stage 160 represents the transit required to get the smart packaging system 10 to its ultimate destination. Information exchanged at the local transit stage 160 can include local transit information 162, such as hospital or surgery center location, truck number, delivery time, handling instructions, and invoice number. During local transit, if any aspect of the smart packaging system has been recalled, the information exchanged can include, for example, a return address, and the smart packaging system 10 can be recalled and returned for assessment and/or disposal.

The seventh depicted stage in the supply chain 100 is the hospital stage 170, which can include one or multiple beacons 102G. The hospital stage 170 represents the hospital or surgery center in which the surgical instrument 14 will be used during a surgical procedure. If local transit is able to deliver the smart packaging system 10, local transit will deliver the smart packaging system 10 to the hospital where it can be stored within the hospital until needed. Information exchanged at the hospital stage can include hospital information 172A, such as operating room (OR) number, storage location, and item count. If local transit is not able to deliver the smart packaging system 10, such as for a recall, the smart packaging system 10 can exchange recall information 172B, such as a return address for the smart packaging system, and a warning with information related to the recall.

The eighth depicted stage in the supply chain 100 is the OR stage 180, which can include a beacon 102H. The OR stage 180 represents an operating room that will use the surgical instrument 14 that is part of the smart packaging system 10. Information exchanged at the OR stage 180 can include OR information 182, such as OR room number, procedure kit details, device number in the total devices needed for the procedure, surgeon information, and patient information.

Information described at each of the stages in the supply chain 100 is exemplary only and does not represent an exhaustive list of the information that can be exchanged at a given stage.

In general, the tracking of surgical instruments can be important for determining a variety of factors regarding the instrument itself. These factors can include prior historical events, such as transportation date or sterilization dates, which can affect the operating parameters of an instrument. Additionally, the factors can include locational data of the instrument, along with the location of any corresponding accessories, which can be used in conjunction with the instrument. An example of corresponding accessories can include the staples for a stapler. Traditional tracking of this information is disjointed, and the continuous stream of data collection does not flow along a singular path from the manufacturer, to the end user, and in some cases, back to the manufacturer. This can lead to disjointed and incorrect information being passed from one stage of the supply chain to another, without correction. This can lead to increased errors and inefficiencies by an end user when performing a surgical procedure.

As such, it is beneficial to include a singular data path that travels along the supply chain, with the instrument. However, while some instruments include power sources and transceivers, and can transmit and receive data with some alteration to their systems, many instruments can be analog, and do not include any form of data transmission. In order to ensure any pertinent data is recorded and stored, the packaging, which an instrument is stored and transported in, can include a transceiver and memory in order to record and store data relevant to the instrument stored in the packaging. In combination with the HUB system described above, the packaging can record and edit metadata directed to the instrument, and also communication with other packaging in the vicinity to direct a user to both proper operational parameters, and also corresponding instruments and accessories.

As stated above, data can be used to relay additional information related to an instrument contained within a packaging to a user. One form of data storage can be in the form of a serial number containing a large density of information. The individual readable bits of data contained within the smart packaging can have multiple layers embedded within them, where each layer yields different information, and additional digital information can be communicated to and from packaging for deep data or metadata transfer within the product identifiers.

Figure 5:
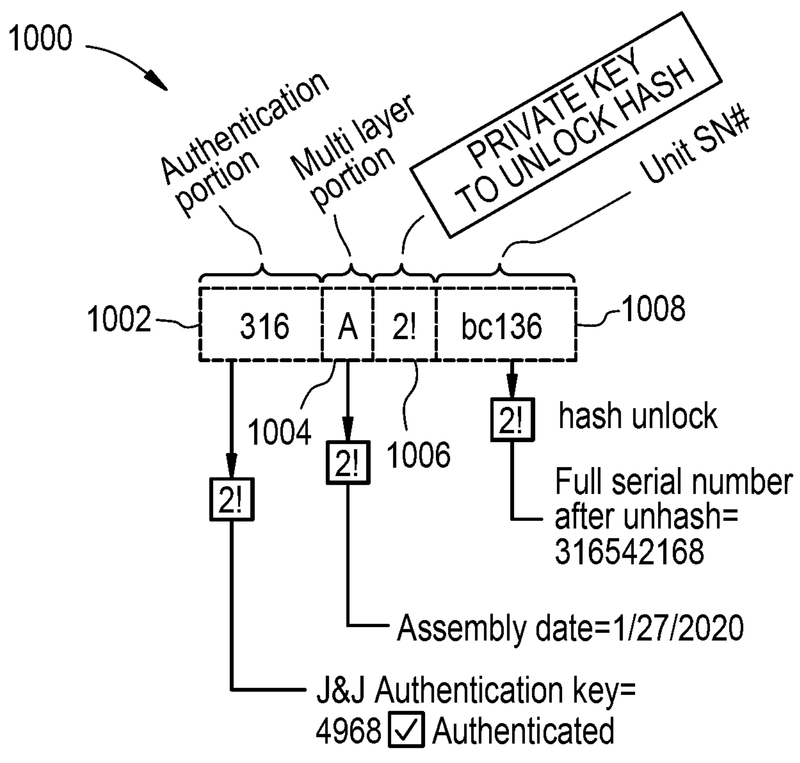
FIG. 5 is a schematic view of a serial number for a smart packaging system containing a surgical instrument according to an embodiment.

An example of this can be seen in FIG. 5, where a cryptologic combination of static identifiers and functions is used to allow a serial number arranged on a packaging to store additional data about the instrument and packaging itself. Increased data density of the characters of the serial number can act as unique product identifier, while also communicating functional aspects of the product to aid in establishing communication or setup of the digital device with the HUB 50. The serial numbers arranged on a packaging can use a combination of alphanumeric characters and symbols that hold more information in a more dense and secure form to enable the packaging and product ID to serve multiple combined uses. Additionally, the use of hash encryptions can multiply the number of combinations by having several of the first characters used to define the key of the hash encryption. A hash function is a mathematical function that converts a numerical input value into another compressed numerical value. The input to the hash function can be of arbitrary length with an output thereof always being fixed in length. A hash function as described herein can be used as an encryption/decryption component of the known key. The hash function can be used to encrypt and compress data stored on a smart package by using a mathematical equation and a password to reduce the data field in size, thus embedding more information. For example, the packaging and product ID can have all meta data stored within the serial number and the device, and can include a key which can use a hash function to remove that decompress and unencrypt the serial number. The rest of the characters in the serial number can be used repeatedly to create multiples of the primary number to substantially increase the number of unique identifiers. For example, the serial number under one hash decryption can define operational constants of the product. Under a separate hash decryption, the serial number can define assembly & parts tractability. Additionally, all of the characters and symbols of the serial number in native format can provide the unique identifier of the packaging itself to the HUB 50. In this way the product data, its metadata, and its unique identifier can all be embedded within the serial number itself allowing the serial number to inform a user of both what instrument is in the packaging, and how to use the instrument all at the same time. This can also result in non-sequential serial numbers from one product packaging to the next due to the intensity of data within the serial number.

As shown in FIG. 5, a serial number 1000 can be positioned on a packaging, such as the smart packaging system 10. The serial number 1000 can include authentication portion 1002, multi-layer portion 1004, key portion 1006, unit serial number portion 1008. The key portion 1006 can be used to perform a hash algorithm decryption on the other portions in the serial number 1000 in order to derive additional data from the unit serial number portions 1008. For example, using the key portion 1006, the full serial number for the packaging can be derived from the unit serial number portion 1008. Additionally, the packaging can be authenticated by deriving an authentication code from the authentication portion 1002. For example, while the serial numbers for different packages are different, the decryption password or private key can be the same across packages of a given product. Accordingly, an authentication code can be derived from the authentication portion 1002 using the universal decryption password or private key to extract both the serial number and any embedded meta data on the device in question within the serial number (e.g., calibrations data). The multi-layer portion 1004 can also be derived to provide additional information, such as the assembly date of the instrument within the packaging.

In addition to embedding data about a product within a packaging, a serial number 1000 can also have embedded HUB 50 commands and triggers within the serial number. When a serial number is scanned into the HUB 50, a portion of the serial number can be configured to update HUB 50 operating code, or trigger an update or data retrieval for the HUB 50 in anticipation of interconnection with new systems. Additionally, use of the serial number can be used as a means to update operational parameters of the control algorithms for the operation of actuators of the digital system. These operational parameters can include sub-system adjustment parameters, capabilities of the product, and device compatibility among systems. The serial number can also be used as a return label or ID number as a means for both traceability, as well as the forces, operation, and/or issues encountered by the device for product inquiries.

The metadata stored in the packaging can also relate to the initial calibration, assembly, manufacturing, packaging, or sterilization of the product. Any data impacting component performance can be linked to the packaging serial number. Documentation resulting from the timing, operators, lines, environmental or storage conditions of assemblies or components that can have impact on overall device performance can be attached at context to the primary serial number, batch stamp, or production data, and be recorded as historical data points. Examples of types of data stored can include assembly line ID or user ID of the product assembly, and environmental parameters during manufacturing. Manufacture or sterilization can have impacts on operability, irradiation cycles for sterilization, since irradiation degrades performance of the plastics, and too many runs through sterilization can jeopardize performance and durability. Additionally, humidity exposure during instrument manufacturing and shipment that can impact operation of the instrument.

Figure 6:
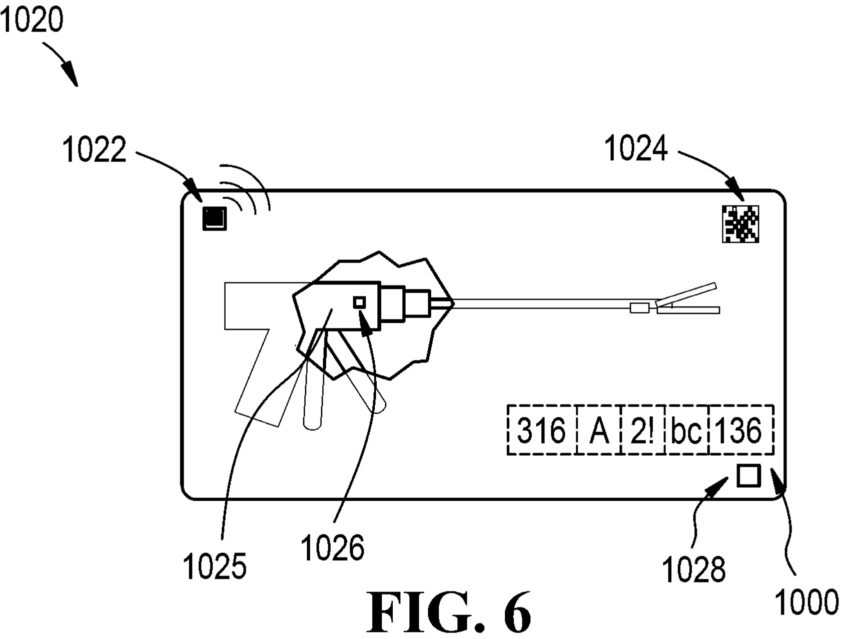
FIG. 6 is a schematic view of a smart packaging system containing a surgical instrument, according to an embodiment.

In some aspects, stored data in packaging can be retrieved by the HUB 50 through a transceiver or smart device creating a channel with a transceiver in the packaging. As depicted in FIG. 6, the packaging 1020 can include a transceiver 1022 and an instrument 1025 arranged within the packaging. The transceiver can be an RFID tag, which can be read by an external device to provide information about the packaging or instrument therein. Additionally, the packaging 1020 can include scanable codes 1024 and 1028, along with the serial number 1000. The scanable codes 1024, 1028 can be scanned by an optical sensor to access additional information about the packaging 1020 and instrument 1026 stored in a cloud database. A scanable code 1026 can also be arranged on the instrument itself, which can be scanned through the clear plastic of the packaging 1020.

With the packaging being configured to store the data as outlined above, the packaging itself can modify the stored metadata in the packaging the data as outlined above, the packaging itself can modify the stored metadata in the packaging as the packaging moves through the supply-chain. In an embodiment, the documentation of any modification of the metadata can be recorded by the packaging in order to optimize the performance of the instrument within the packaging. Examples of recordable historical events include multiple passes through sterilization, or multiple passes through a factory. This is due to degradation of the instrument with multiple sterilization processes or uses. Therefore, when the metadata stored in the packaging is retrieved, the metadata can provide adjusted operating parameters to a user based on the history of the instrument itself in order to optimize the instrument's performance.

For instruments such as staplers, cartridges can be rebuilt and reloaded. The stapler and cartridge themselves can be agnostic to the fact that the cartridge is a reloaded cartridge, since the instruments themselves do not contain any sensors or electronic components to record such events. However, the packaging which the instruments are stored in are able to record these processes. For example, the serial number for a given stapler could be assigned or re-assigned as a part of the staple loading process. The re-assigned serial number can include meta-data relating to the loading process (e.g., which machine is being loaded, what time the machine is being loaded, what staple size and shape, etc.). This re-assigned serial number can be printed onto the labeling and/or the cartridge. In some embodiments, the re-assigned serial number can simply include new data being added to the end of the previous serial number indicating it was reloaded and the meta data for that as well. Additionally, for harmonic devices and transducers, similarly to as described above, the number of burn-in attempts can be recorded to give the instrument the ability to recognize how many uses it has performed, including during manufacture and testing. Even further as an example, robotic arms and tools can be reprocessed, which can lead to degradation. Storing and tracking metadata in their packaging can enable the understanding of the full picture of a product's usage data. This data can then be used to generate updated operating parameters, which can be provided to a user at a later stage in the supply chain progression, as described in detail below.

Figure 7:
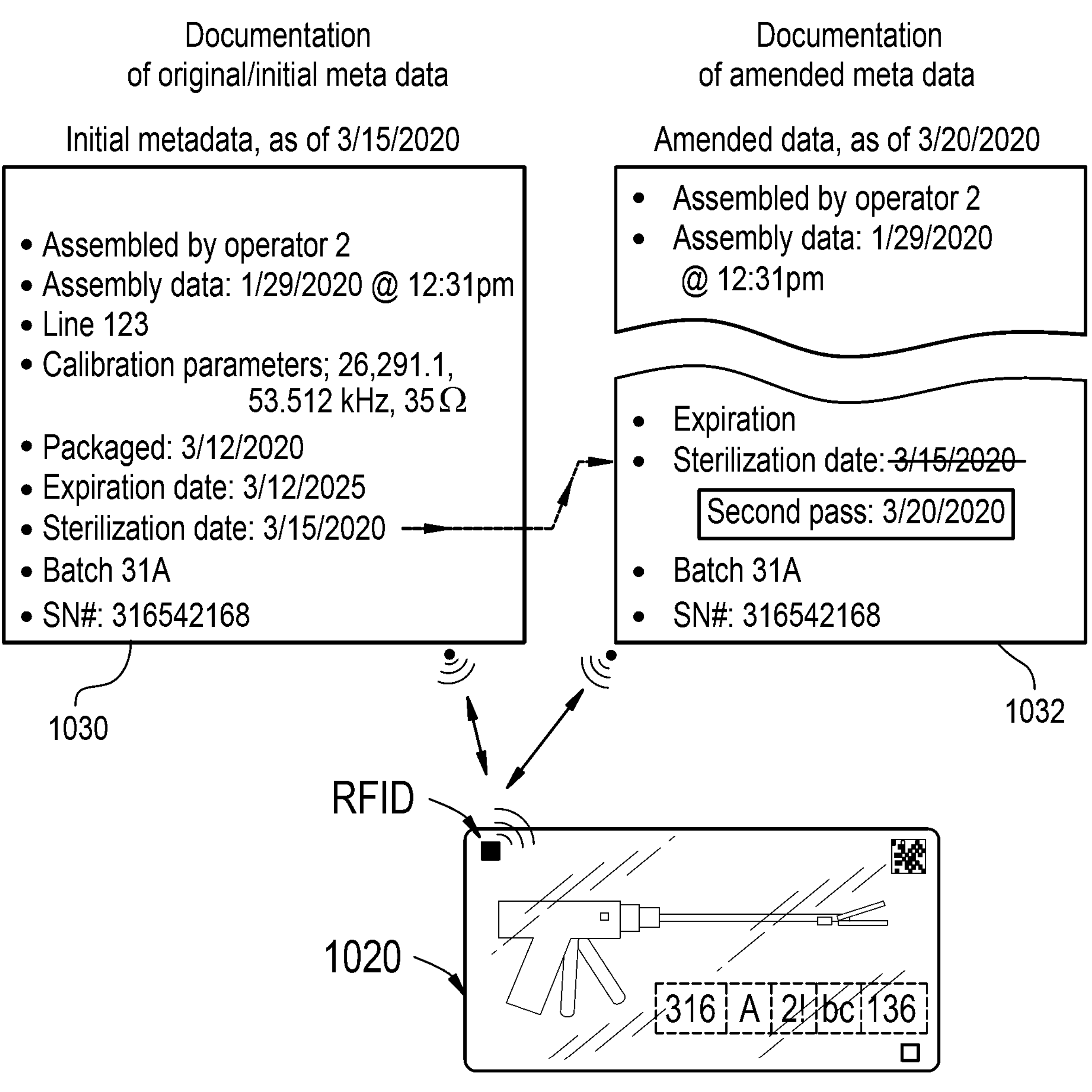
FIG. 7 is a schematic view of the smart packaging system of FIG. 6 displaying a first set of information and a second set of information.

As stated above, in addition to serial numbers on a packaging, the packaging can include scannable codes to access additional information stored in a cloud database. As depicted in FIG. 7, once scanned on a smart device, a window 1030 can appear on a display of the smart device, which can contain information about the packaging 1020 and the instrument, such as assembler, assembly date, line number, calibration parameters, packaging date, expiration date, sterilization date, batch number, and serial number. However, as stated above, the metadata of the packaging 1020 can be amended based on what processes the instrument has undergone. For example, in some circumstances, instruments can be reclaimed for later use, and if the instrument is being reused, the window 1032 will show the second sterilization date, while also showing the first sterilization date. This way, a user and the system 10 can know that plastics contained in the instrument may have degraded due to radiation exposure over multiple sterilization passes.

As stated above, a serial number on the packaging can be used to store a large density of data using encryption. In some embodiments, the serial number can also include scanable QR codes or bar codes to pull even more stored data from a remote data source, where the scanable code can be altered by the HUB 50 to show different codes, which pull up different sets of information when scanned, as the packaging moves through the supply-chain. In combination with cloud database access, the scanable code can be used to access the history and operational data of an instrument. Methods of scanning can include manual scanning, active wireless transmission by capable devices, direct detection, geo-fencing, BLE beacons, and by surgical step. The packaging or device shroud/exterior can contain a singular, printed code that can be scanned by a smart phone or scanner attached to the HUB 50. When scanned, the code opens a portal website that allows the user to see or report quality information to a cloud database. Real-time recall alerts can also be stored on the cloud database. These alerts are sent out by the manufacturer to prevent a recalled instrument from being used in a surgical procedure. Additionally, the cloud database can be used to log complaints received from healthcare personnel about an instrument that was used during a surgical procedure.

By using the scanable codes on packaging, a user can access a cloud or HUB database. Data stored in the cloud database can include device characteristic and manufacturing history tracking of the instrument. For example, harmonic device data can be recorded into the cloud database (i.e., frequency, impedance, capacitance, etc.). Additionally, historical data points can include motor and electrical characterizations, staple height, and frictional coefficient in a moving shaft, such that algorithmic adjustments can be made to optimize device based on this recorded device data. An example of optimization can include a stapler cartridge recommendation based on the device assembly data of a stapler which a surgeon has chosen to use for a surgical procedure.

In one embodiment, the expiration status of an instrument can be passively determined by arranging a printed barcode on a shaft or jaw of stapler or energy device in view of a laparoscope. Video imaging from the laparoscope can be used to check expiration in real-time during the surgical procedure, and then alert user. This kind of monitoring can function in a number of ways, such as relying on a specific visual indicator present on an object to constantly track that object. For example, a packaging of surgical needles can include a specific pattern or scanable code that is related to an expiration date. A camera included in the systems can be relied on to visually monitor an area for that specific pattern, even at multiple angles. When the pattern is detected, the expiration date of the instrument object can checked in real-time.

In addition to a single scanable code being positioned on a packaging, which can be scanned to provide a user with additional information about the instrument within the packaging, multiple scanable codes can be used to determine the compatibility of sub-assemblies contained in separate packaging. In some embodiments, packaging codes are accessible on the exterior of a packaging while sealed so that information is communicated and indicated prior to opening the packaging to maintain sterility in the event a different option is chosen once compatibility is checked. The first code of a combination sub-device prompts the user to scan the code of the compatible sub-device, so that a comparison can be made between the two devices. In the event compatibility is not determined after scanning of the codes, the user can be able to override the request if desired. The compatibility check can prevent use if a non-authentic device combination is detected (for example, a non-authentic reload being used on an authentic stapler, or a reprocessed tip prevented from being used on an authentic handpiece, or vice-versa).

Bluetooth low energy ("BLE") beacons can be employed for another kind of technique for object monitoring. The BLE beacons can repeatedly transmit a signal that other devices can detect, such as via a radio signal. The signal can comprise an encoded message of letters and numbers transmitted on short intervals, which can be used for specific transmissions and to encode specific messages and data. The BLE beacons can be used to register products currently located in an operating room, and they can also be used to communicate status changes of detected objects and products. Additionally, multiple communicating devices can be disruptive and lead to interference between signals transmitted by those communicating devices. A number of techniques can be employed to minimize disruption. For example, the smart packaging system 10 can contain one or more methods to alter a bandwidth of its transmissions, as well as multiple methods of communication. Some of the methods of communication can rely on the internal power source 15 of the smart packaging system 10. Some methods can derive power from an external source, such as an external electro-magnetic field, such as with near field communication (NFC), or with an external wired connection, such as via a USB cable or the like.

The smart packaging system 10 can rely on RFID tags to communicate with other devices, but if RFID becomes unavailable, the smart packaging system can rely on secondary means of communication. For example, NFC and RFID could be combined such that, with RFID, power is obtained from an external field and broadcasting only occurs when the system is prompted. With the NFC, an antenna can be used, and upon activation, other systems, such as WIFI and battery systems, can be deactivated to save power.

Figures 8, 9:
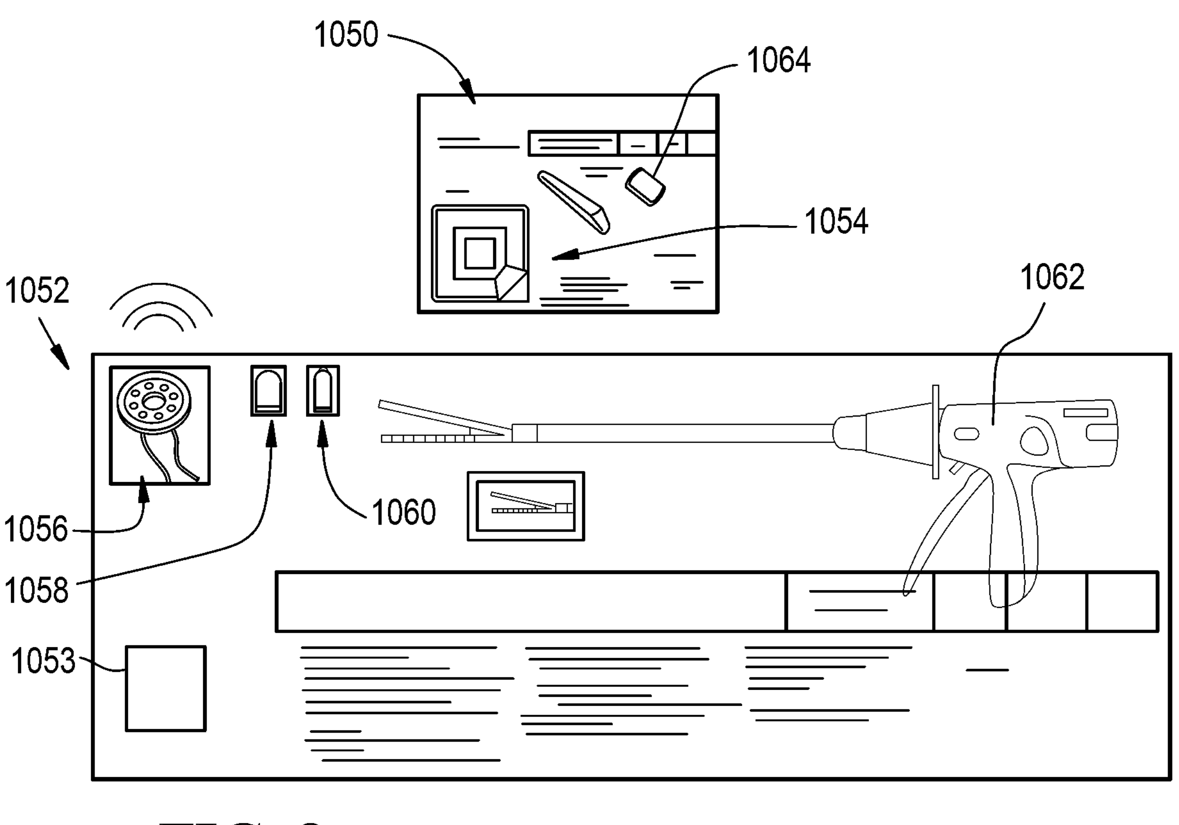
FIG. 8 is a schematic view of a smart packaging system containing a surgical instrument, according to an embodiment.
FIG. 9 is a graphical representation of the degradation of a transducer.

In addition to having a user physically scan codes present on the packaging, active and passive compatibility checks can be contained within the packaging. As depicted in FIG. 8, a packaging 1052 with an active electronic chip 1053 (powered by a battery positioned within the packaging), and another packaging 1050 with a passive electronic chip 1054 (e.g., an RFID tag) can actively communicate with each other to indicate device compatibility to a user between the instrument 1062 and the accessory 1064. In this instance, the active chip 1053 and passive chip 1054 act as transceivers which can communicated with surrounding sub-assembly packaging when in close proximity to automatically check compatibility among the sub-assemblies. Additionally, one of the packaging, for example the packaging containing the power supply, can also include a feedback device in the form of a speaker 1056, or different colored LEDs 1058, 1060 in order to give feedback on compatibility to the user. When the two packaging 1050, 1052 are in close proximity, the feedback devices can be activated to alert a user to the compatibility of the subassemblies.

In one embodiment, both packaging can include passive chips, which have to be scanned by a user in order to determine compatibility between the sub-assemblies. The scanning of the passive chips can be performed in a way that has minimal disruption on a surgical procedure. For example, the chip in each packaging can be scanned automatically upon entry to an operating room through a central transceiver, such as the HUB 50. An active global geo-fence is another kind of technique for object monitoring. An active global geo-fence can be assigned to a specific geo-physical location, and all objects passing through that fence can be tracked. A combination of systems can be combined to monitor objects passing through this fence, such that the combination of systems can detect objects in a combined device or as separated elements. Based on this determination, the system 10 then gives visual and/or audible feedback on compatibility of the devices. Additionally, an optical sensor, such as a camera on a smart device, can be used to take a picture of the packaging or scan a scannable code or RFID tag with the smart device in order to determine compatibility. Additional types of technologies that can be used in the packaging can include Radio Frequency (RF), High Frequency (HF), Ultra High Frequency (UHF), Near Field Communication (NFC), where passive read range up to ~25 m, and active read ranges are up to ~100 m.

In addition to determining compatibility between sub-assemblies, the system 10 can also provide a list of additional compatible devices in order to optimize the operation of an instrument. The system 10 can determine alternative sub-assemblies if the system 10 determines that a chosen sub-assembly, while it may be compatible, is not the best choice for a specific procedure. Additionally, the list of compatible components can include trade-off options between speed, cost, complications (e.g. RF vs. endocutter) of different compatible sub-assemblies. Examples of types of compatible comparisons for staplers can include reload staple material compared to a subsequent reload, compatibility of shaft to handle, or handle to adapter, or shaft to adapter, or buttress compatibility. Additionally, examples of types of compatible comparisons for energy device can include harmonic energy device blades to handpiece, energy RF device or blade to handpiece, energy device to generator, return pad to generator.

In addition to determining compatibility between already-selected sub-assemblies, the system 10 can also provide indicators to a user for selecting a compatible sub-assembly. The system 10 can include smart storage that highlights the product codes that are compatible with instruments/sub-assemblies already pulled. The smart storage can utilize the feedback devices already present in the packaging of a sub-assembly. For example, each packaging can have an LED that lights up in response to a wireless signal sent through a smart device when looking for a specific compatible component (e.g., select on a phone app that a user is looking for reloads for a specific stapler, and then all the different types of staple cartridge reloads compatible with that stapler can light up while on the shelf in a storage area.

In an embodiment, instead of a smart device being used, the packaging of the stapler can also include a transceiver in the packaging. When a user activates the transceiver via a switch or button, all the reload packaging that are compatible and connected wirelessly to the system 10 light up. In an embodiment, augmented reality can be used to locate compatible packaging using a headset or smart device app that highlights the product codes that are being searched for or that are compatible with products already pulled for use in a surgical procedure.

While it has been stated above that the packaging can include a chip for storing data, a chip can instead be present on the instrument itself, and not tied to the packaging. For example, a staple retainer can include an RFID tag that stays attached to the stapler while in use.

In addition to checking compatibility, the system 10 can be used to determine if an instrument has been repackaged. The system 10 can read a serial number or scanable code on the packaging, and compare it to a database that contains all the matching combinations of a particular instrument and its corresponding packaging. If the instrument is put in a new packaging, the codes will not match, and the system 10 can let the customer know the device has been repackaged through visual or audio feedback. This can also enable a manufacturer to reprocess devices and update the database with the new packaging codes.

Based on the data being stored in the packaging, and accessible via a cloud database, the system 10 can offer suggestions to users in order to increase operational efficiency. Suggestions can be made to a user based on the scanned instruments within a packaging. The information can be based on cloud data available from a large body of users, or can be tailored to be a dataset just from that single user so that the suggestions are built upon that individual's experiences and skill level. For example, the system 10 can recommend reloads or products based on historic usage by a specific surgeon, specialty, procedure, and/or patient demographics. Additionally, the system 10 can include virtual kitting recommendations based on procedure, patient conditions, and/or surgeon preference (based on what is recommended or what the surgeon has been using in past similar experiences). Even further, the system 10 can provide statistical data corresponding to what other surgeons have used during a similar operation. Algorithms can be used to provide a product recommendation or common practices to the surgeon (e.g. 30% of cases start with a green reload on a sleeve).

In an embodiment, the system 10 can notify a user if they are using a product in a method inconsistent with typical usage (e.g., incorrect type of reload in a first sleeve firing). Additionally, the system 10 can determine if an energy device is operating outside of recommended operation parameters since the energy device was scanned earlier in the procedure. Even further, the system 10 can provide a recommendation for a shaft length based on patient characteristics or port placement, specifically in robotic procedure where port placement and anatomy location are known.

As stated above, the system 10 can operate to provide additional data corresponding to instruments selected for a surgical procedure. In addition to determining capability, the system 10 can also determine optimized operational parameters based on the historical usage of the instrument. Specifically, the system 10 can provide optimized operating parameters based on an intended use to initiate optimized device customizations. For example, a surgical stapler can have operating parameters which are customized due to the use of an unused cartridge, instead of using a reloaded cartridge, where the system 10 can enable the device to accommodate the degradation of a reloaded cartridge. In a reloaded cartridge, the sled degradation over use can impact staple height and therefore be coupled with wait time or speed to minimize the impact on staple height. For an endocutter, the system 10 can determine a custom device calibration that detects losses for the endocutter to allow the system 10 to instruct motor operation differently in order to provide the user a consistent device response to differing tissues even across variable build instruments.

Additionally, the system 10 can provide energy device customization, where custom details of the transducer are provided to the generator/HUB 50 to update the control programs. This customization is due to the fact that each transducer has slightly different harmonic and electronic aspects due to its construction and prior usage which are recorded within the transducer as a calibration and operational parameters. These parameters enable the generator to adjust its drive parameters to customize performance for each individual combination.

Examples of operational parameters which can be adjusted include an operational temperature or impedance/frequency data as a means for limiting or calibrating thermal implications. Also, the blade construction and specific dimensions/tolerances/connection of the blade to a transducer can be provided to the system 10 to update the control programs of the endocutter. Even further, the initial clamp force measurement can be used to update the control programs.

The system 10 can also be used to compare expected measurements with actual measurements. For example, a transducer has a specific number of cycles for which it can be energized. The transducer has internal electronics that counts each re-use, where a re-use is counted after a predetermined amount of time energized is exceeded so that just plugging a transducer in and immediately unplugging it does not trigger a use count. When a transducer is used, the system 10 can capture total power through the system 10, record frequency, impedance, capacitance, phase margin, power displacement.

Once a transducer is used, it must be sterilized. However, improper sterilization energy, such as non-OEM sterilization, can degrade the internal components of the transducer, using up a portion of the "full life" of the product. In order to prevent improper sterilization, a UPC code can be placed on the transducer and recorded in a cloud database. This can be cross-referenced with the generator which the transducer is used with. For example, if the generator interacts with the transducer 26 times, but the cloud database has only recorded a single use of the transducer, then the transducer can be disabled though the HUB 50 not allowing a generator to provide power to the transducer, due to unknown degradation of the internal components.

Additionally, the packaging can include a memory card for expanded parameters to guarantee proper sterilization. For users to receive credit for a reused transducer, the memory card can be plugged into a generator USB port, which will tag the memory card with the use cycles, and give the user a generator credit for their next transducer. The memory card can be sent back to the manufacturer in return packaging. Also, the system 10 can track the last use output data of the transducer recorded by the transducer, and if the transducer's last recorded use is not identical to the stored last use in the cloud, then the transducer can be disabled by the system 10.

In an embodiment, the generator can cross-check the serial number of the transducer attempting to be used in conjunction with the generator from a list of approved serial numbers stored in a cloud database. Every time a transducer is used with a generator, the use cycles are tracked and added to the cloud database. Additional data recorded by the generator and uploaded to the database can include the transducer serial number, device serial number, frequency, impedance, displacement, capacitance, amount of cuts, mode, and power level.

As stated above, sterilization of a product can lead to degradation. In order to determine if a component has been sterilized, the phase margin of the transducer can be tracked over time, as depicted in FIG. 9. Phase margin is an aspect of an ultrasonic transducer that defines the device's ability to seek and hold the natural frequency of the wave-guide and blade in use. As the transducer ages, the phase margin shifts. In this case the generator can write the information of its last use into the data in the transit labels to allow the next use or the recovered transducer to help with remanufacturing at the factory. As shown in graph 1090, after each sterilization, the phase margin of the transducer declines. If the component is sent back to a manufacturer, a phase margin decline can be seen upon testing, and compared to previously recorded data from that component and/or requirement/limit. Additionally, the phase margin of a transducer can be determined by monitoring the temperature of a transducer during a sterilization procedure to track and adjust life of the transducer accordingly.

Upon connecting a device to a generator, the phase margin is recorded to the cloud database. After each sterilization cycle, the phase margin declines in the transducer. If the transducer is retuned to a manufacturer, the phase margin parameter can be updated in the database after testing for reusability. If a transducer is plugged into a generator, and the recorded phase margin is not within a threshold range of what was anticipated, the generator will not supply power to the device, since this is evidence of non-OEM sterilization.

In an embodiment, in order for the packaging to communicate with the system 10, the packaging can include a multi-level power source to enable variable data communicability through at least two transceivers having a high power level and a low power level. A supply of power can be included in the packaging circuitry to enable interaction of the transceivers and the system 10. Two wireless communication arrays can be positioned in same packaging. Communication of portions of the data can be accomplished via a first system transceiver, like an RFID tag, and a second, more complex transceiver connected to the power source. In some embodiments, only one transceiver can be active at a time. The power source contained within the packaging can be a wireless receiver for energy that is transmitted to the packaging, or the power supply can be in the form of a battery. In some embodiments, the power supply is rechargeable.

In order to determine what type of instrument is contained within a packaging, the use of physical landmarks within the packaging can be used to enable device recognition. Types of physical landmarks can include specific patterns at certain locations about the packaging or the instrument itself. For example, a stapler can include a scanable pattern which can be determined by a camera in the vicinity, such as an operating room or a laparoscope. The usage of physical landmarks of measures, calibration, or predefined device length can aid in the system 10 determining a type of a device/packaging. In some embodiment, a discrete set of predefined points can be used to determine the location of an instrument by optical sensors, such as cameras in an operating room. In some embodiments, multiple cameras can work together to observe a packaging and instrument in order to determine the type of instrument being used.

In some embodiments, the location tracking of an instrument, using the techniques described herein, can be used to help prevent inadvertent activation of the instrument. For example, the system 10 can determine that a harmonic device was placed on a table in an operating room. This can be accomplished, for example, with the use of accelerometers in the devices. Alternatively, when a camera sensor is used, the camera sensor can be configured to track the location and movement of the device. In this case, if the movement of the device ceases for a predetermined amount of time, as perceived by the camera sensor, the tracking algorithm can be configured to determine that the device has been set down. Therefore, if the trigger is activated inadvertently while the device is on the table, the device will not activate since it is not being held. Additionally, since the system 10 can determine the location of a device using cameras (or other methods), a graphic user interface (GUI) or interface displayed on a screen displaying the surgical site through the camera of a laparoscope or the like can be adjusted based on the dimensions of the instrument. In some embodiments, the visual system 10 recognizes the instrument and/or packaging serial number in order to correctly configure the GUI.

In addition to tracking of an instrument using physical landmarks, the packaging can include calibration and parameters for the local interpretation of the digital raw data feeds from the device within the packaging. For example, the packaging can determine if a trigger on the surgical instrument has been fully depressed. The trigger can be tracked continuously through its full range of motion (e.g., via a Hall effect sensor rather than a contact switch), which can be used to scale the output range to the mechanical limits of the actual trigger motion (including tolerance stack, implying different devices have slight differences in full range of motion). This recorded data can then be used to adjust energy output/energizing via thresholds of program chosen transition points.

In some embodiments, the system 10 can authenticate packaging and instruments based on received input. The authentication process can include the system 10 generating unique, randomized serial numbers by using an algorithm based on the current date to generate the serial numbers. If an unrecognizable/inauthentic serial number exists on a packaging, then the system 10 will provide an alert. In one embodiment, if multiple cartridges in a row have sequential serial numbers, then the system 10 will verify the authenticity of the cartridges if there is an anomaly in a serial number of one of the cartridges. If a "knock-off cartridge" is determined to be currently in use, and is unusable, for example, the cartridge is identifying as a 45 mm staple cartridge, but instead is a 60 mm staple cartridge, then the instrument will not fire. However, if a generic cartridge is determined to be usable with an instrument, a generic operation mode can be activated on the instrument to enable use with the generic cartridge.

Figures 10, 11:
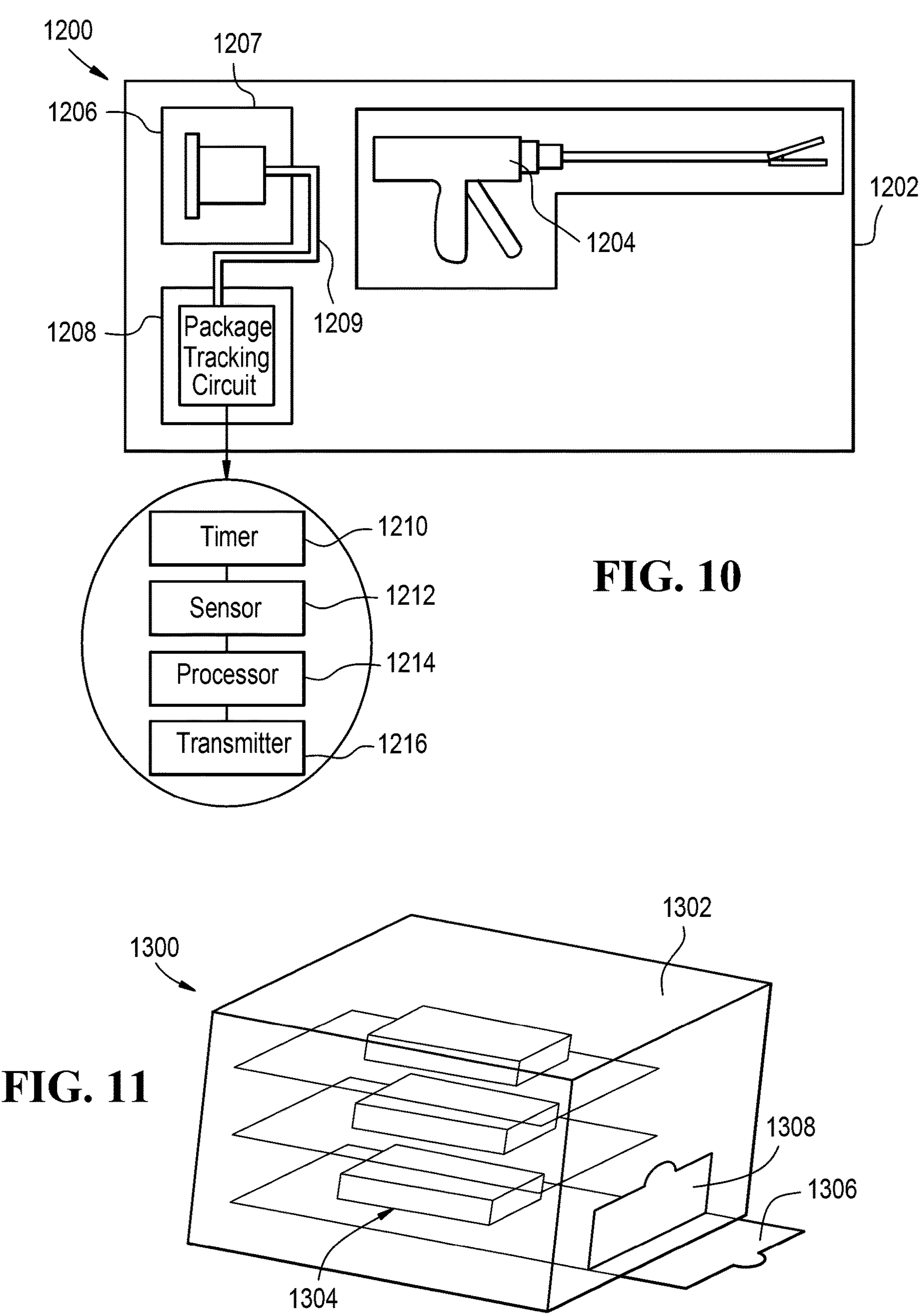
FIG. 10 is a schematic view of a smart packaging system containing a surgical instrument, according to an embodiment.
FIG. 11 is a perspective view of a smart packaging system, according to an embodiment.
Figure 12:
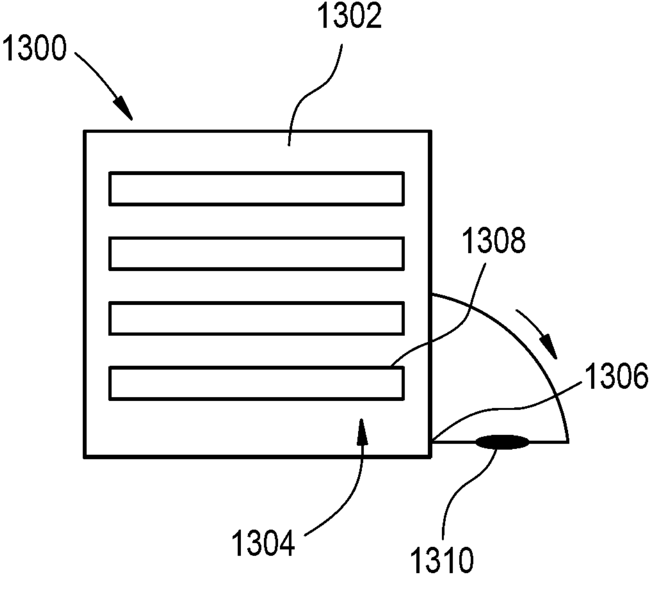
FIG. 12 is a side view of the smart packaging system of FIG. 11.
Figure 13:
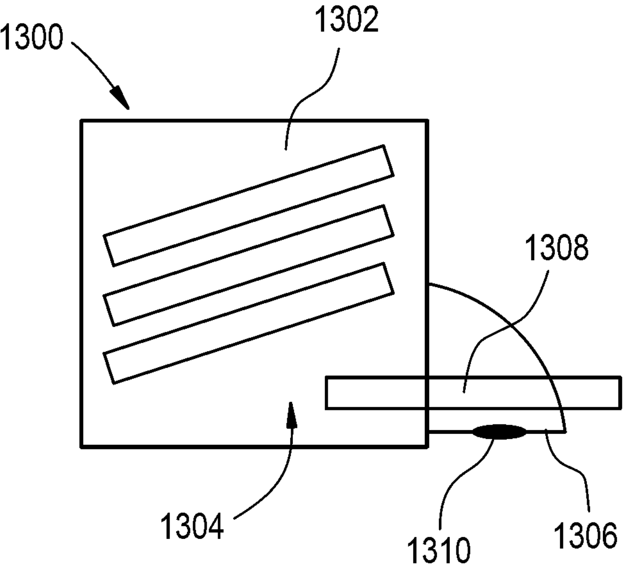
FIG. 13 is a side view of the smart packaging system of FIG. 11.

As stated above, the packaging 1200 can include a transceiver and a power supply. In an embodiment depicted in FIG. 10, the packaging 1200 can include a housing 1202, a sterile medical device 1204, and a power supply 1206, where the packaging uses the contained power supply to operate a control circuit 1208 associated with the packaging to sense and indicate a status of packaging 1200 or instrument 1204 contained in the packaging. The power supply 1206 can be primary cell battery or rechargeable cell battery. The battery itself can have a dedicated compartment 1207 within a tray of packaging 1200, and the compartment 1207 is outfitted with conductive contacts 1209 to draw energy from the battery to power the control circuit 1208 associated with the packaging 1200. The control circuit 1208 can include a timer 1201, a sensor 1212, a processor 1214, and a transceiver 1216. Sensor 1212 can also be arranged within the packaging to measure external factors which can affect the instrument within the packaging. The packaging can be constantly powered, intermittently sensed, or powered on demand.

With the packaging constantly powered, the battery compartment circuit is always in contact with battery and powers a sensor without interruption for tracking sensors or transceivers that record shipping or storage events throughout a lifecycle. For example, temperature history, a countdown timer for shelf life tracking, accelerometer for shock/impact levels.

In an aspect, with the packaging intermittently powered through sensing, a duty cycle timer inside packaging turns on an element for only portion of a cycle. For example, to save battery life, part of the packaging tracking circuit will turn a sensor within the packaging on for 5 minutes of each hour to track events that are not expected to suddenly occur, like temperature. For more sudden events, the part of the circuit that powers an accelerometer for example can be activated more frequently, or be activated by a change in status where it uses external motion of the packaging to turn on the sensor itself.

With the packaging powered on demand, the connections between the battery and packaging circuit only happens at a purposeful time when activated by a user. It can be a switch or electronic signal to begin transmitting and tracking. This can conserve battery capacity and be used for specific on-demand indicators like showing battery level, or for time-sensitive activities like connecting to a HUB 50 for a procedure. When activated, the packaging can actively look for HUB 50 system and automatically register the device into a hub tracking system to identify the device type, verify the expiration status, and check for compatibility against other associated accessories (like between staplers and cartridges). Electronic activation can occur through a passive tag (RFID or NFC) in the packaging that is held a short distance away from a battery and antenna. When activating this tag, the user physically changes a configuration of the packaging to send current through a circuit to ping the tag, which then sends a signal wirelessly out from the packaging to a HUB 50 or other receiver systems containing packaging or device information.

Figure 14:
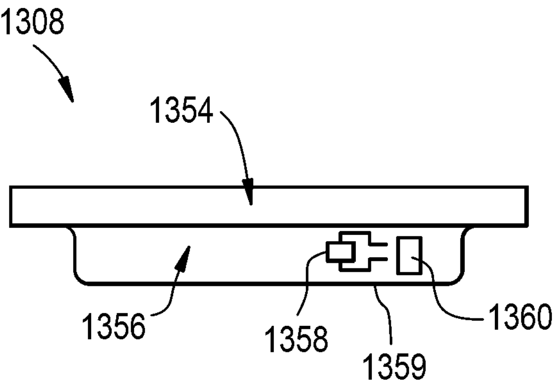
FIG. 14 is a schematic view of a smart packaging system, according to an embodiment.
Figure 15:
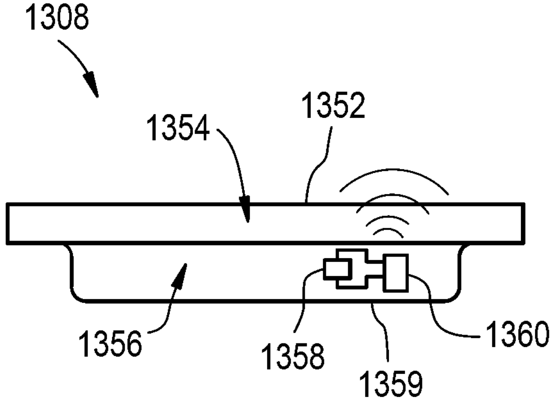
FIG. 15 is a schematic view of the smart packaging system of FIG. 14.

An example of activating the power supply of the packaging can be in the form of a magnetic switch. As illustrated in FIG. 11-FIG. 15, a magnetic element inside the sterile packaging can be configured to slide between first and second configurations. A transport system 1300 can include a transport container 1302, which contains a plurality of packaging 1308. The packaging 1308 are stacked on top of one another such that, when a packaging 1308 is removed from the lower compartment 1304, the next packaging slides downward into the compartment 1034. The compartment 1304 can be accessed by opening the door 1306. When desired, the user places a magnet 1310 in close proximity to exterior of packaging 1308 and slides the element to change the configuration and connect the battery. As shown in FIG. 14, the packaging 1038 can include an instrument compartment 1354, a battery compartment 1356, a battery 1358 having leads 1359, and a control circuit 1360. The magnet 1310 can be embedded in the door 1306, and positioned in a way to slide the battery 1358 and leads 1359 towards the control circuit 1360 in order to complete the circuit, while removing the packaging 1308 from the transport container 1302. In one embodiment, a spring-loaded switch can be held by a magnet in the storage container, and then when a packaging is removed from the storage container, the magnet stops holding the circuit open. In an aspect, the spring is made from folded parts of the packaging itself.

In an embodiment, the packaging has a dedicated battery separate from the device arranged within the packaging, where the dedicated batter is only present to power the packaging. In one aspect, the battery compartment may contain an indicator for packaging battery power, for example a small LED that indicates there is sufficient current remaining in the dedicated battery to transmit information.

In an embodiment, the dedicated packaging battery may contain a pull tab to protect the battery from draining when not desired, for example during shipping. The pull tab remains inside sterile barrier, but is accessed by manipulating an exterior surface to allow covering of battery contacts until a user removes the tab.

Figure 16:
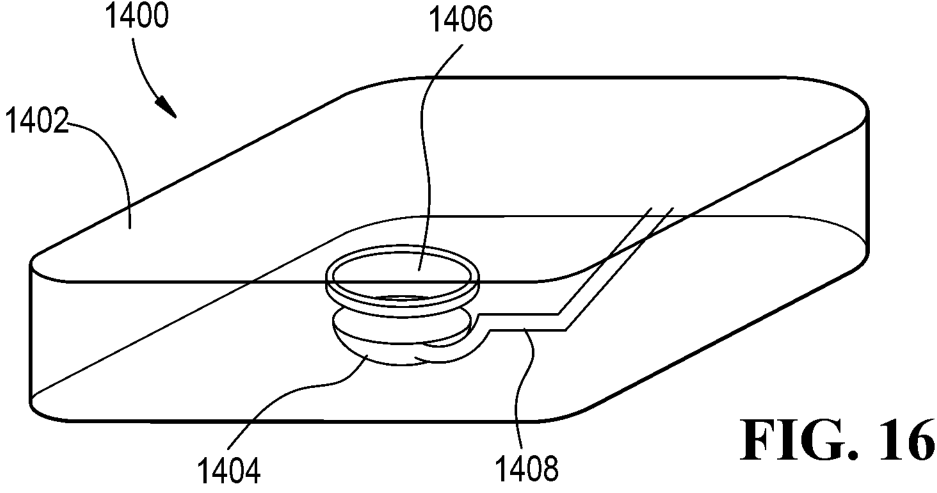
FIG. 16 is a perspective view of a smart packaging system, according to an embodiment.
Figure 17:
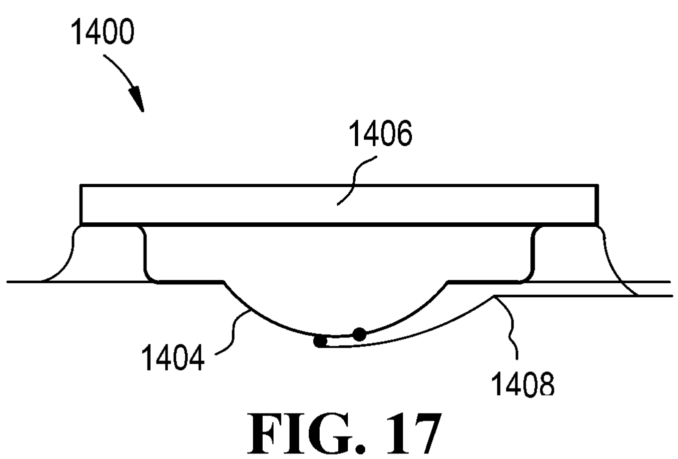
FIG. 17 is a side view of the smart packaging system of FIG. 16.
Figure 18:
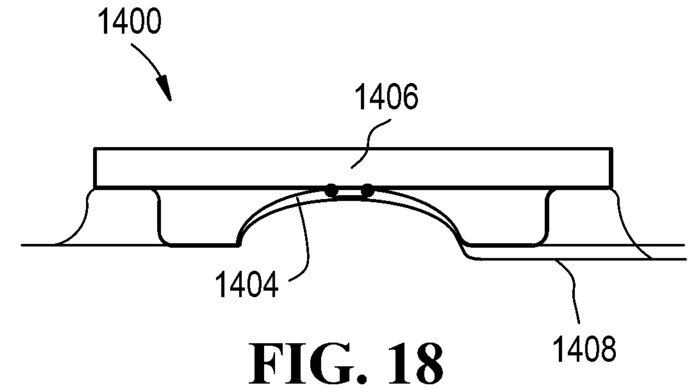
FIG. 18 is a side view of the smart packaging system of FIG. 16.

As depicted in FIG. 16-FIG. 18, in another embodiment, a packaging system 1400 can include a packaging 1402. A bubble 1404 can be formed in the packaging 1402. A portion of the blister of the packaging 1402 is formed into a bubble 1404 that allows it to be popped in or out. The first configuration, depicted in FIG. 17, where the bubble 1404 is popped out allows the battery 1406 to be disconnected from the circuit leads 1408. In the pressed-in second configuration, depicted in FIG. 18, the bubble 1404 is pressed into the packaging 1402, which causes physical connect between the battery 1406 and the leads 1408, allowing a circuit within the packaging 1402 to be powered. The bubble position may be reversible to connect or disconnect battery 1406 (for example, if unintentionally pressed or to deactivate signal transmission). In an embodiment, the packaging battery may be rechargeable battery that is able to be charged quickly to a level needed to transmit a signal. The charging can be accomplished by placing the packaging on a wireless battery charger using wireless charging technology in the operating room as part of the normal process of bringing devices into the operating room.

As stated above, the packaging can contain a battery within the packaging to power transceivers and sensors. However, a battery exposed directly to radiation during a sterilization process can be damaged. In an embodiment, a packaging contains a separate, connective and reactive power source, which is electrically isolated in a sub-packaging compartment. This separate power source provides power to transceivers and sensors but can be removed during a sterilization process.

In an embodiment, a power source can be connectively re-engagable. For example, two physical bodies that need to be reconnected within the sterile boundary of the packaging itself, such as a loose battery and battery plug in different compartments, can be reconnected by manipulating the outside of the packaging. In an embodiment, insertion of a primary packaging into a secondary packaging can connect together a battery and its corresponding leads to provide power without compromising sterility. The act of combining primary and secondary packaging physically connects the packaging and mechanically completes the circuit. A user can push them together, and then slide them to break away a plastic area that will open the connectors to allow the circuit to be complete.

In an embodiment, the power source is reactively re-engagable. For example, all of the wires can be built into the packaging wall that includes a plastic pull-tab, which acts as a barrier to interrupt the electrical connection between the power supply and sensors until the tab is removed. During gamma radiation, a current is created within conductive components via the radiation that can destroy sensitive electrical components within circuits. Therefore, the circuits are configured to remain disconnected while the packaging is receiving gamma radiation. Additionally, in an embodiment, instead of a plastic tab, a container of acid can be arranged between two barriers such that once the container is crushed, the chemical acid dissolves the barrier and fuses the circuit.

While the packaging has many primary uses, as outlined above, such as compatibility and authentication-checking processes, the packaging can also be multi-use packaging that has a secondary use independent from the first use. A primary use of the packaging can be the product identification. In an embodiment, a secondary use of the packaging can include reuse prevention and detection, device disassembly assistance, return the device return, device cleaning (such as including a basin or chemical to clean a harmonic blade when in use by a user or post procedure prior to return), quick trouble shooting, and/or assembly or disassembly guidance. The assembly or disassembly guidance, for example, can include separated compartments with text/images of where components need to be placed for return, and include replaceable components with a guide as to how to replace/install those components.

In an embodiment, a single scanable code can be contained on both a device and a packaging. A single code is printed onto two different substrates, where each substrate contains an incomplete portion. The first portion may be printed on a clear, or see-through substrate. There can also be a position datum needed to orient substrate 1 to substrate 2 below it. Substrate 2 contains the missing information of the single code, so that when scanned, the complete code is provided only when both are present and oriented correctly. The code is needed to activate or track a device system. Without a code, the system is not registered. Each scanable static codes can be arranged on at least two components (for example, the packaging and the endocutter), where each code can be read separately to provide one set of information (such as the date of manufacture, the type of device, the expiration date). But when the two codes are stacked or arranged to be read together, additional information can be accessed (like authentication code that assures the device has not been reprocessed). For example, a packaging tray, which is nearly transparent, has a partial QR code printed thereon. The device within the packaging has a portion of the QR code, so that the two codes added together form the complete code.

The system 10 can also prevent the reuse of data stored in the packaging. A single use sensor can be arranged on the packaging, and is destroyed when the packaging is opened. The packaging peel can contain part of the sensor or circuit that is broken when the packaging is opened. For example, a lid peels away from plastic tray, where the circuit is partially printed on the tray, with an interruption in the area that the lid is glued. The lid contains a conductive filament that interconnects that interruption while sealed. The act of peeling will remove the jumper and interrupt the circuit. In an embodiment, the lid can contain a bar code is printed on an area of the lid that is peeled, so that code is no longer legible once the packaging is opened. The code is positioned on two different sides of a pouch, in the glued zone. Once the code is broken and illegible, the device cannot be scanned into the procedure, limiting its ability to take advantage of digital solutions information.

The system 10 can include features that are altered once the packaging is opened. In an embodiment, opening the packaging can expose an initially concealed extra bar (as part of bar code) that can change how it is read. In an embodiment, a portion of the bar code can become visible after sterilization. The use of photochromic inks can be sued as well on the exterior of the packaging. Additionally, in an embodiment, oxidization chemical exposure can cause a change to a bar code, where the packaging includes a portion of a bar code that is environmentally sealed from both the interior and external environment. This portion is purged during packing with an inert gas, and opening exposed the portion to $O_2$ or $CO_2$, which erases the ink and causes the bar code to change.

In some embodiments, as explained herein, the packaging itself can contain a display in order to display the stored metadata within the packaging. In this embodiment, a smart packaging label only displays information necessary to a current user (i.e., a packaging can store all kinds of information about its own supply chain, but a doctor only gets information relevant to the doctor). The packaging "knows" what to present to the doctor based on various factors, such as its location in the supply-chain progression, interactions with certain personnel, the type of surgical procedure to be performed, and corresponding accessories and instruments.

Generally, the smart packaging system 10 can provide a user (e.g., transportation worker, customs officer, warehouse personnel, hospital/facility staff, medical team, etc.) with information concerning itself. The information can be conveyed by the smart packaging system 10 in a number of ways, as will be described below, and the information conveyed can be dependent on a number of factors, including: composition, contents, present location, destination, identity of the user, authorization level, functional capabilities, external stimuli, and more.

Generally, the smart packaging system 10 can be aware of its historic and future states, as well as its intended usage, throughout its lifecycle. In essence, the smart packaging system 10 can possess an awareness of itself during its lifecycle. This awareness can result in the smart packaging system knowing: 1) its location within a facility supply chain; 2) when it has been received at a medical facility; 3) when it enters a stockroom or storage at the medical facility; 4) when it is requested for usage in a medical procedure; and 5) when it enters an operating room for the requested medical procedure. Each of these aspects of awareness will be further described.

Locations that trigger different labels or transmittals of information, generally, can include: warehouse, storage, transit, sterilization, supplier distribution center, mode of transit, customs, regional distribution center, local delivery, healthcare facility receiving, store room, operating room, repackaging in an operating room, healthcare facility cleaning/sorting, disposal, reuse, return shipping, etc. In some embodiments, the smart packaging system 10 is configured to store its intended destination (e.g., a specific hospital), and to document and store a historic record of its travels as it progresses toward its intended destination. Additionally, the smart packaging system 10 can be configured to determine its location within the pathway to its intended destination.

Based on the packaging location in the supply-chain, the label can present different information to a current user. A supply-chain progression is depicted in FIG. 4. In an assembly stage 110, the display can show the parts, acceptance of parts date, revision number, and calibration/certification data (for components and device). In a warehouse stage 120, the display can show sterilization data, batch number, stock, FIFO date, and shelf location. In a transit stage 130, the display can show a sender address, truck ID, received address, handling instructions, customs data (e.g., declared value), bill of assembly, and generic title. In a distribution stage 150, the display can show a shelf location, number of number in stock (e.g., 1 of 5, 2 of 5, etc. currently in stock), model number, FIFO data, and expiration date. In a local transit stage 160, the display can show a location, truck number, delivery time, and distributor invoice. While in a hospital stage 170, the display can show an order number, storage location, and item number of number in stock. While in an operating room stage 180, the display can show an operating room number, procedure time, surgeon ID, patient ID, and device number of number in procedure (e.g., 1 of 4 pieces required for the given procedure).

In some embodiment, data displayed can be capable of updating along the supply-chain, and is readable by the user without connecting to a HUB 50 or aggregation system 10. For example, an E-ink display that when exposed to a wireless power source (e.g., external electric field) is capable of updating the display from the internal electronic stored information or sensed aspects of the packaging. The use of a separated device battery can be used to update the electronics. It can have separate circuit that can have a portion of the packaging that the user interacts with to create a short term power connection that allows the display to update.

While the display can update on the packaging based on where the packaging is in the supply chain, the packaging can also include environmental adaptation designs to provide additional information to a user. In an embodiment, a portion of the label has aspects that are adaptive to environmental conditions of the interior or exterior to the packaging. For example, portions of the label can update due to chemical or thermal reactive events, such as exposure of the contents to different aspects of temperature, humidity, light exposure, or energy radiation. This causes the element to change based on either a maximum short-term dose, or a cumulative exposure level.

Figure 19:
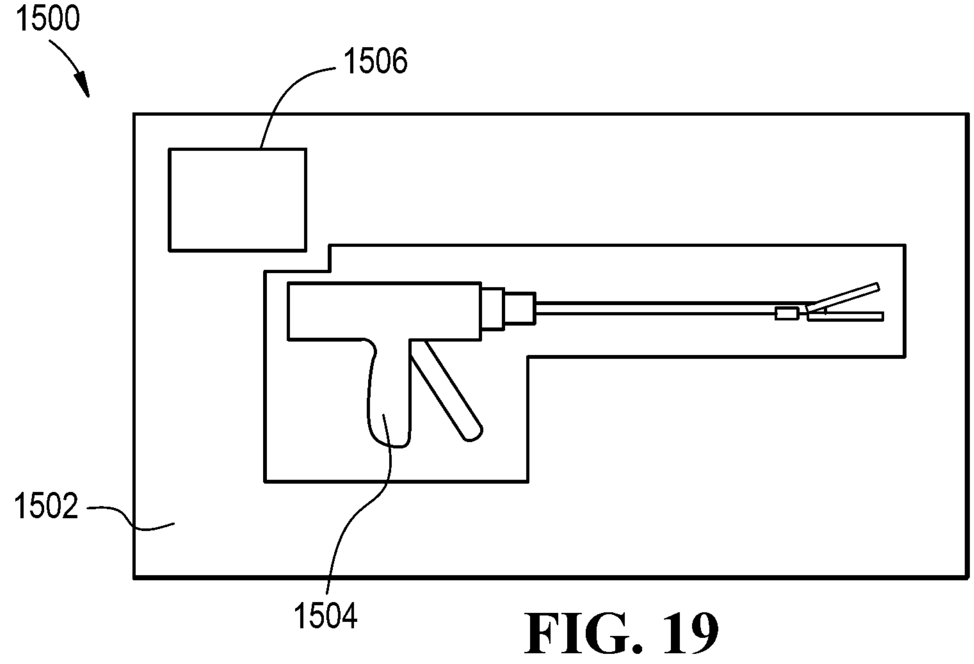
FIG. 19 is a schematic view of a smart packaging system, according to an embodiment.

In addition to electronic sensors, a simplified mechanical sensor can be used in combination with or as a replacement to a powered sensor on a packaging. As depicted in FIG. 19, a mechanical, non-continuously powered sensor 1506 can be arranged within a packaging 1502 of a packaging system 1500. The sensor 1506 can be arranged in a separate compartment from the instrument 1504, can be activated by a user action at a specific time (such as when the device is scanned before use, or when placed into an inventory), and can be used to instantly check the integrity of the packaging and instrument. Types of physical indicators that take the place of powered sensors can include an accelerometer.

Figure 20:
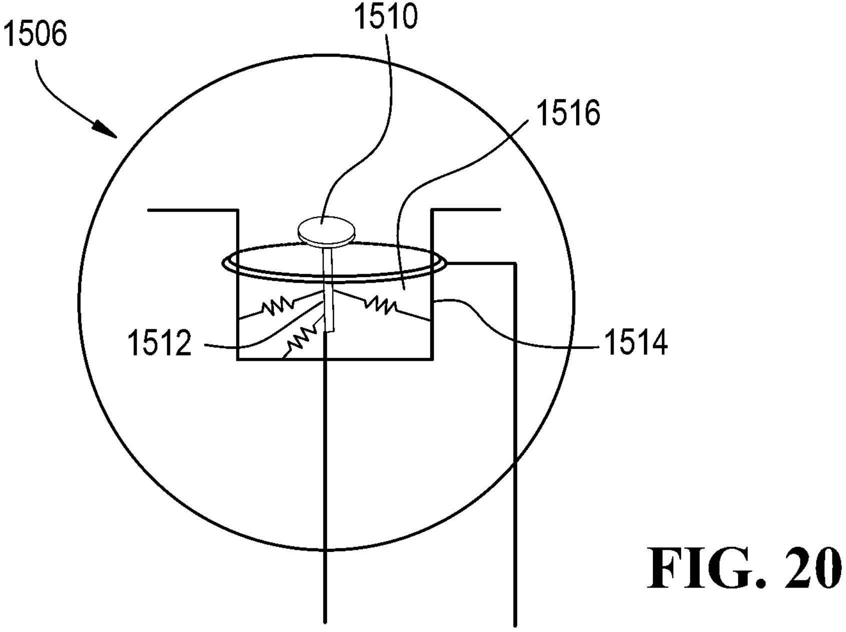
FIG. 20 is a side view of a mechanical sensor, according to an embodiment, of the smart packaging system of FIG. 19.
Figure 21:
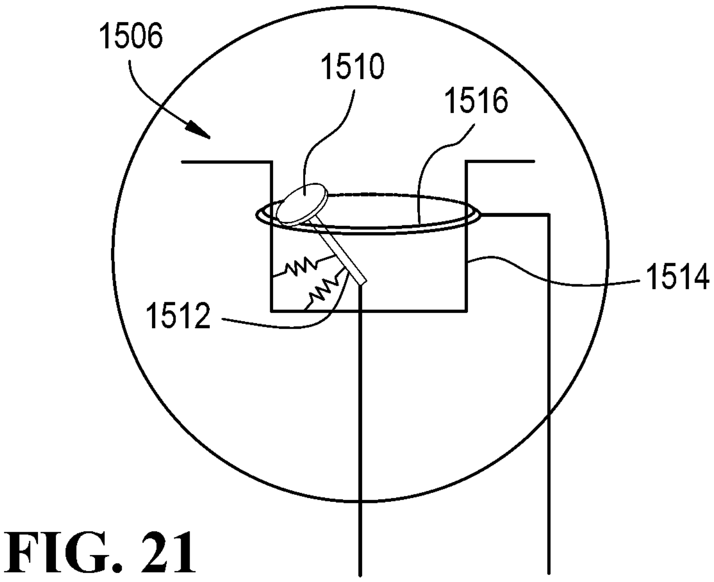
FIG. 21 is a side view of the mechanical sensor of FIG. 20.

As depicted in FIG. 20-FIG. 21, in an embodiment, the sensor 1506 can include a magnet 1501 arranged on a post 1512, which is moveable in all directions. Connected to the post 1512 are springs 1516, which help keep the post 1512 centered relative to a surrounding wall 1514. The surrounding wall 1514 is made of a ferrous material such that if the magnet 1510 comes within close proximity to the surrounding wall 1514, the magnetic force will overcome the force applied to the springs 1516, and the magnet 1510 will stick to the surrounding wall 1514. With the magnetic 1510 connected to the surrounding wall 1514, a user can visually see the packaging has experienced a high-force load above a threshold amount. Additionally, the packaging can include a circuit which is completed once the magnet 1510 contacts the surrounding wall 1514, sending a signal to a memory within the packaging, recording the exceed threshold as a historical data point. The alert can be presented to a user once the packaging transmits any form of data, or can show directly on a display on the packaging.

In another aspect, a spring can be suspended between a circuit and a battery to trip in a force is applied to the packaging beyond a threshold level. The spring can disconnect the battery from the circuit if an experienced force was beyond a threshold amount.

Figure 22:
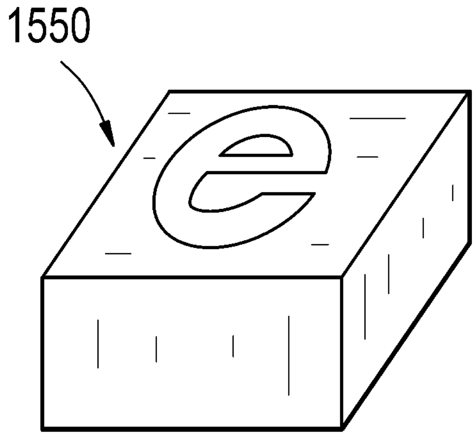
FIG. 22 is a perspective view of mechanical sensor of a smart packaging system, according to an embodiment.
Figure 23:
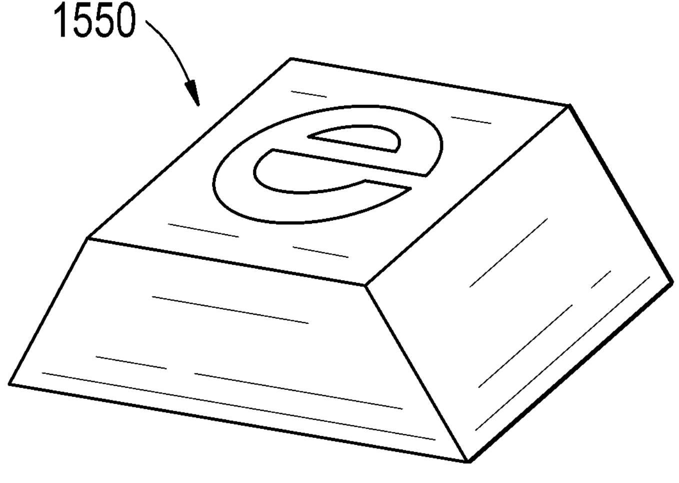
FIG. 23 is a side view of the mechanical sensor of FIG. 22.

As depicted in FIG. 22-FIG. 23, in another embodiment, a thermally-reactive element 1550 can be used. The thermally reactive elements 1550 can be in the form of a wax-like element arranged within a packaging. The wax-like element 1550 can originally have a specific shape (i.e., rectangle, circle, or specific logo), shown in FIG. 22, that will alter in form, such as melting, warping, and/or cracking, if the packaging is exposed to temperatures outside a minimum or maximum threshold, shown in FIG. 23.

In another embodiment, an optical UV detector can be used on the packaging. A thin, clear polycarbonate can be arranged in the packaging such that when exposed to light, the polycarbonate yellows or clouds when a threshold of UV is exceeded. Thickness of such polycarbonate sheets can be in a range of 0.015" to 0.025". As explained above, UV exposure can weaken certain components of the packaging and surgical instrument, e.g., certain plastics can become very brittle. UV exposure above a certain threshold can warn an operator that the packaging and/or surgical instrument may be compromised.

Powered alternatives to these mechanical devices can include an accelerometer included in packaging, a thermometer within the device powered by battery in a packaging, and optical sensor to record UV exposure, a barometer, a humidity sensor, or a GPS.

As stated above, each packaging can include a transceiver in the form of an RFID tag to facilitate communication with external systems (e.g., to allow a stock room to know where a given device is). An RFID tag needs close proximity for energization. In the context of a stock room layout, as a user walks down an aisle of a stock room with a smart device, the RFIDs in the packaging arranged on the shelf can be energized in order to read the data stored on the RFID tag. This passive reading can be used to notify user of recalled products. The HUB 50 can utilize an interface or stock room layout that powers the display on the packaging to change the E-ink display on the packaging to indicate to the user to not use that specific instrument.

The display itself can have a multi-level menu which can be navigated in order to provide addition data not shown on the initial screen of the display. Additionally, the display can include a scanable code which can direct a user to additional information stored in a cloud database. Some of this information can be region-specific information, such as optimal device performance instructions, other surgeons or experts that use this device in your area, top users in region, local rep contact info, personal message/video from assembly line, device built or component sourced from a local area, connection to Real-world evidence (RWE) studies, complaint automation, geo-location (language specific), a universal complain icon, mistaken use credit offering (send a replacement, for example), rewards points, disposal guidance, compatible devices such as buttresses, reloads, trocars, best practices documents, YouTube instructional videos, or marketing materials. RWE is a method of gathering information from medical records and other sources in order to determine how a treatment works in practice. The display can also include multiple languages, which can be changed automatically through GPS, or a user command. For example, the product reads English when it is in the US prior to shipment, giving all English shipping instructions, and as soon as the packaging detects it has landed in Germany for example, the display language immediately switches to German.

While it is stated above that packaging can provide additional data through the use of a smart device or scanner, other packaging themselves can also provide additional data to one another such that a combination of packaging provides more information together than an individual packaging can provide separately. For example, a user can gather several packaging together, where the packaging can give the user information related to the packaging as a set (i.e., compatibility, or operating limits), which one packaging cannot do alone.

As depicted in FIG. 24-FIG. 28, the system 10 can ensure cooperative packaging are interlocking, nesting or seat together for a surgical procedure. The system 10 can detect the color, shape, outline, theme, and features of a device once the packaging is scanned or enters the operating room using any of the methods described herein. This allows the system 10 to confirm that all pulled packaging contain compatible instruments and accessories. The displays on the packaging themselves can also provide a message to a user that a specific cartridge needs to be used with a specific stapler. This way, a user can collect all necessary, compatible packaging prior to a surgical procedure starting.

Figure 24:
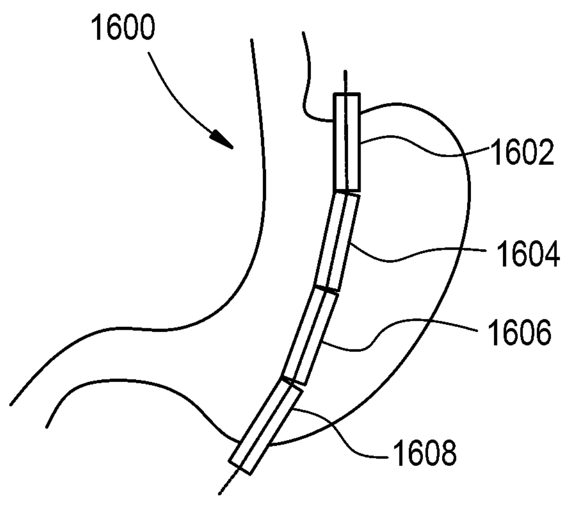
FIG. 24 is a schematic view of a gastric sleeve surgical procedure.
Figure 25:
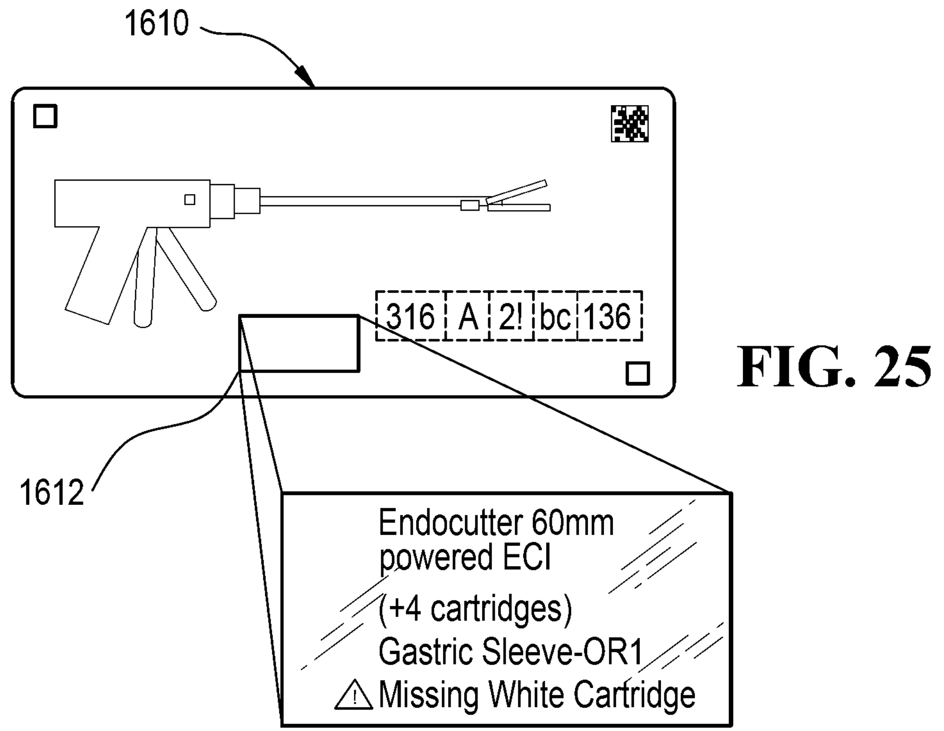
FIG. 25 is a schematic view of a smart packaging system, according to an embodiment.

FIG. 24 is a schematic view of a stomach 1600 undergoing a gastric sleeve surgical procedure. In order to perform the surgical procedure, a plurality of staple sets 1602, 1604, 1606, 1608 need to be stapled to the stomach. Due to the volume of staples used in the procedure, the stapler will be required to be reloaded in order to complete the procedure. Additionally, the staple set may be different depending on their required operating parameters corresponding to their location on the stomach 1600. As depicted in FIG. 25, to ensure the proper staples are used with the correct stapler, when a user collects a packaging 1610 containing a stapler, a display 1612 on packaging can be altered by the system 10 to alert the user to collect the corresponding staples as well, and for what surgery the stapler and staples are needed for. The display 1612 can also display to a user the corresponding location where the packaging 1610 can be arranged in operating room.

Figure 26:
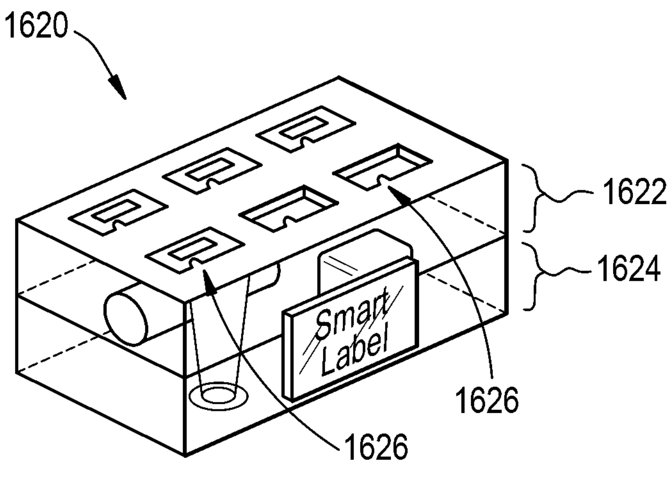
FIG. 26 is a schematic view of a loading device of the smart packaging system of FIG. 25.

In order to ensure the proper staple set are used, in an embodiment, an operating room may contain a table 1620 having openings 1626, which packaging 1610 seat into in order to confirm all compatible products are present in the operating room. As depicted in FIG. 26, the table 1620 can include an upper portion 1622 and a lower portion 1624. In an embodiment, the accessories, such as staples can be arranged in the top portion 1622, and the instruments which utilize the accessories can be arranged in the lower portion 1624. The table 1620 can also be used for loading the accessories into the instruments.

Figure 27:
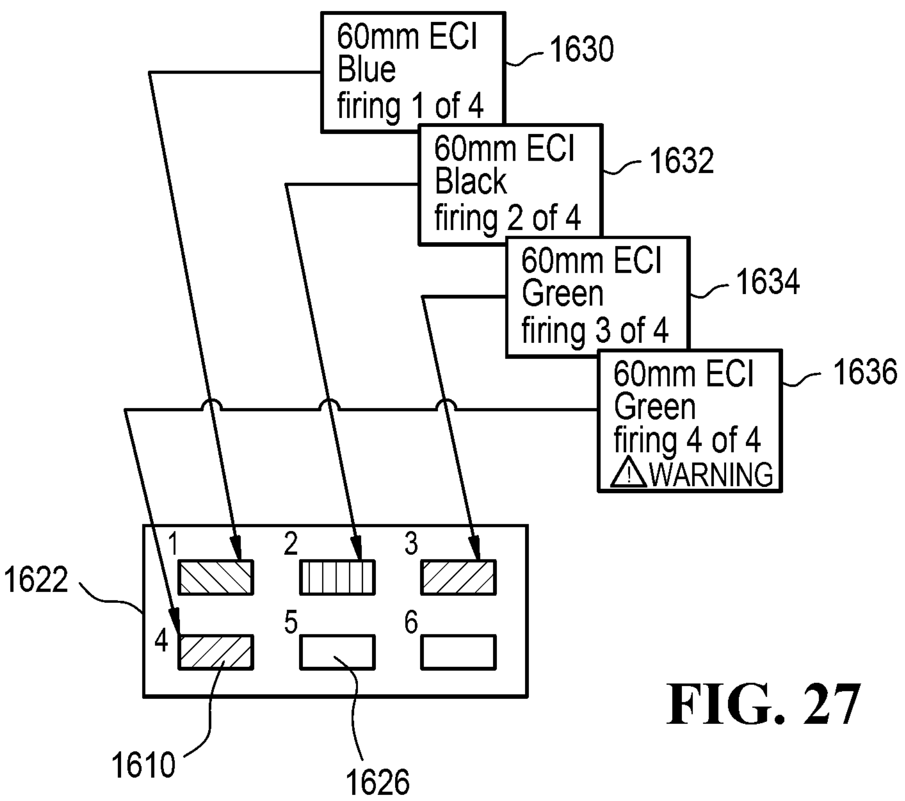
FIG. 27 is a schematic view of the loading device of FIG. 26.
Figure 28:
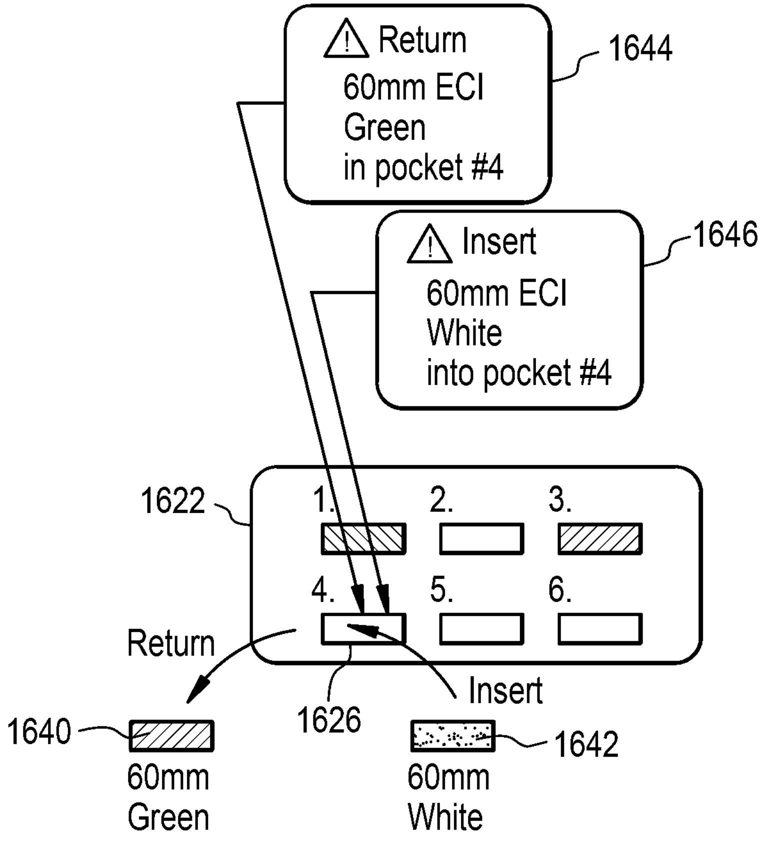
FIG. 28 is a schematic view of the loading device of FIG. 26.

As depicted in FIG. 27, once a packaging 1610 is arranged within an opening 1626, the displays 1630, 1632, 1634, 1636 on each packaging can provide to a user the firing order of each staple cartridge, and can also provide a warning if an incorrect packaging is arranged in the table 1620. Additionally, as stated above, there may be multiple compatible options of an instrument to use during a procedure. As depicted in FIG. 28, two compatible packaging 1640, 1642 can be used for a procedure. The display 1644 of the packaging 1640 can provide a user with a warning to return the packaging 1640 to the opening 1626 if a user has removed the packaging 1640. Simultaneously, the system 10 can alter the message provided on the display 1646 of the packaging 1642 to insert the packaging 1642 into the opening 1626, since both packaging 1640, 1642 can be used for a surgical procedure.

After a surgical procedure is completed, the system 10 can track combinations of product usage pairings to optimize patient outcome. The system 10 can provide feedback, such as a comparison of what packaging were pulled compared to the packaging that are returned/unused. This information can be used to inform hospital administrators of device use trends. In order to provide more data, when a packaging is returned without being used, a reason can be included on why it was pulled/returned. Examples of messages can include (1) device was pulled as a "just in case" (2) redundant pull (3) usually I use it (4) found alternate device.

Certain illustrative implementations have been described to provide an overall understanding of the principles of the structure, function, manufacture, and use of the systems, devices, and methods disclosed herein. One or more examples of these implementations have been illustrated in the accompanying drawings. Those skilled in the art will understand that the systems, devices, and methods specifically described herein and illustrated in the accompanying drawings are non-limiting illustrative implementations and that the scope of the present invention is defined solely by the claims. The features illustrated or described in connection with one illustrative implementation may be combined with the features of other implementations. Such modifications and variations are intended to be included within the scope of the present invention. Further, in the present disclosure, like-named components of the implementations generally have similar features, and thus within a particular implementation each feature of each like-named component is not necessarily fully elaborated upon.

Approximating language, as used herein throughout the specification and claims, may be applied to modify any quantitative representation that can permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated by reference in their entirety.

What is claimed is:

1. A manufacturer-sealed sterile surgical packaging containing a surgical instrument configured to be used in a surgical procedure, wherein the manufacturer-sealed sterile surgical packaging comprises a processor disposed in the manufacturer-sealed sterile surgical packaging, wherein the processor is configured to:

record historical data points of the surgical instrument, wherein the historical data points comprise transportation information of the surgical instrument;

determine a degradation level of the surgical instrument based on the historical data points;

determine an altered set of operating parameters based on the degradation level of the surgical instrument; and transmit, via a radio frequency identification tag transceiver, the altered set of operating parameters, wherein the altered set of operating parameters is associated with increased compatibility between the surgical instrument and a surgical accessory.

2. The manufacturer-sealed sterile surgical packaging of claim 1, wherein the processor being configured to record the historical data points comprises the processor being configured to track an amount of sterilization procedures applied to the surgical instrument.

3. The manufacturer-sealed sterile surgical packaging of claim 1, wherein the processor being configured to record the historical data points comprises the processor being configured to track an amount of operations performed by the surgical instrument.

4. The manufacturer-sealed sterile surgical packaging of claim 1, wherein the processor being configured to record the historical data points comprises the processor being configured to track environmental conditions where the surgical instrument is located.

5. The manufacturer-sealed sterile surgical packaging of claim 1, wherein the altered set of operating parameters increases an operational accuracy of the surgical instrument.

6. The manufacturer-sealed sterile surgical packaging of claim 1, wherein the altered set of operating parameters are displayed on a remote device in electronic communication with the manufacturer-sealed sterile surgical packaging.

7. A method, comprising:

recording, by a manufacturer-sealed sterile surgical packaging, historical data points of a surgical instrument contained within the manufacturer-sealed sterile surgical packaging, the surgical instrument configured to be used in a surgical procedure, and the historical data points comprise transportation information of the surgical instrument;

determining a degradation level of the surgical instrument based on the historical data points;

determining an altered set of operating parameters based on the degradation level of the surgical instrument; and transmitting, via a radio frequency identification tag transceiver, the altered set of operating parameters, wherein the altered set of operating parameters is associated with increased compatibility between the surgical instrument and a surgical accessory.

8. The method of claim 7, wherein recording the historical data points comprises tracking an amount of sterilization procedures applied to the surgical instrument.

9. The method of claim 7, wherein recording the historical data points comprises tracking an amount of operations performed by the surgical instrument.

10. The method of claim 7, wherein recording the historical data points comprises tracking environmental conditions where the surgical instrument is located.

11. The method of claim 7, wherein the altered set of operating parameters increases an operational accuracy of the surgical instrument.

12. The method of claim 7, wherein the altered set of operating parameters are displayed on a remote device in electronic communication with the manufacturer-sealed sterile surgical packaging.

13. A non-transitory computer program product storing instructions which, when executed by at least one data processor forming part of at least one computing system on a manufacturer-sealed sterile surgical packaging containing a surgical instrument configured to be used in a surgical procedure, cause the at least one data processor to implement operations comprising:

recording historical data points of the surgical instrument, wherein the historical data points comprise transportation information of the surgical instrument;

determining a degradation level of the surgical instrument based on the historical data points;

determining an altered set of operating parameters based on the degradation level of the surgical instrument; and transmitting, via a radio frequency identification tag transceiver, the altered set of operating parameters, wherein the altered set of operating parameters is associated with increased compatibility between the surgical instrument and a surgical accessory.

14. The non-transitory computer program product of claim 13, wherein recording the historical data points comprises tracking an amount of sterilization procedures the surgical instrument has underwent.

15. The non-transitory computer program product of claim 13, wherein recording the historical data points comprises tracking an amount of operations performed by the surgical instrument.

16. The non-transitory computer program product of claim 13, wherein recording the historical data points comprises tracking environmental conditions where the surgical instrument is located.

17. The non-transitory computer program product of claim 13, wherein the altered set of operating parameters are displayed on a remote device in electronic communication with the manufacturer-sealed sterile surgical packaging.

* * * * *